United States Patent
Xia et al.

(10) Patent No.: US 10,621,756 B2
(45) Date of Patent: Apr. 14, 2020

(54) APPARATUS AND METHOD FOR CORRECTING BIAS IN LOW-COUNT COMPUTED TOMOGRAPHY PROJECTION DATA

(71) Applicant: Toshiba Medical Systems Corporation, Otawara-shi (JP)

(72) Inventors: Ting Xia, Mundelein, IL (US); Jian Zhou, Buffalo Grove, IL (US); Zhou Yu, Wilmette, IL (US)

(73) Assignee: Canon Medical Systems Corporation, Otawara-shi (JP)

(*) Notice: Subject to any disclaimer, the term of this patent is extended or adjusted under 35 U.S.C. 154(b) by 86 days.

(21) Appl. No.: 15/406,089

(22) Filed: Jan. 13, 2017

(65) Prior Publication Data

US 2018/0204356 A1 Jul. 19, 2018

(51) Int. Cl.
- *G06T 11/00* (2006.01)
- *A61B 6/00* (2006.01)
- *A61B 6/03* (2006.01)

(52) U.S. Cl.
CPC ......... *G06T 11/005* (2013.01); *A61B 6/032* (2013.01); *A61B 6/461* (2013.01); *A61B 6/482* (2013.01); *A61B 6/5205* (2013.01); *A61B 6/5211* (2013.01); *A61B 6/5258* (2013.01); *A61B 6/582* (2013.01)

(58) Field of Classification Search
CPC ..... G06T 11/005; A61B 6/032; A61B 6/4441; A61B 6/461; A61B 6/5205; A61B 6/5211; A61B 6/5258; H04N 5/2256; H04N 5/32

See application file for complete search history.

(56) References Cited

U.S. PATENT DOCUMENTS

| | | | | |
|---|---|---|---|---|
| 5,307,264 A | * | 4/1994 | Waggener | G06T 11/006 378/14 |
| 2004/0264626 A1 | * | 12/2004 | Besson | A61B 6/032 378/4 |
| 2006/0066911 A1 | | 3/2006 | Miller et al. | |

(Continued)

FOREIGN PATENT DOCUMENTS

WO   WO 2015/115309 A1   8/2015

OTHER PUBLICATIONS

S. Asif Hussain, et al., "Superior Reconstruction Quality Improvement of CT Image for Bias Correction Variance Measures", International Journal of Computer Application (0975-888), vol. 47, N. 35, Jun. 2012, pp. 22-29.

(Continued)

*Primary Examiner* — Pinalben Patel
(74) *Attorney, Agent, or Firm* — Oblon, McClelland, Maier & Neustadt, L.L.P.

(57) ABSTRACT

A method and apparatus is provided to obtain projection data representing an intensity of X-ray radiation detected at a plurality of detector elements after traversing an object, the projection data being corrected for a baseline offset, correct the projection data by performing a positivity mapping to generate corrected projection data, perform a logarithm operation on the corrected projection data to generate post-log projection data, correct for a bias of the post-log projection data, using the projection data, to generate bias-corrected projection data, and reconstruct an image of the object from the bias-corrected projection data.

21 Claims, 13 Drawing Sheets

(56) References Cited

U.S. PATENT DOCUMENTS

| | | | |
|---|---|---|---|
| 2006/0159223 A1* | 7/2006 | Wu | A61B 6/032 378/18 |
| 2008/0273651 A1* | 11/2008 | Boas | G06T 11/005 378/4 |
| 2012/0177173 A1* | 7/2012 | Xu | G06T 11/005 378/19 |
| 2013/0079626 A1 | 3/2013 | Shmatukha et al. | |
| 2014/0307934 A1* | 10/2014 | Batenburg | G06T 11/005 382/131 |
| 2015/0379745 A1* | 12/2015 | Zhang | G01N 23/046 382/131 |
| 2017/0000442 A1* | 1/2017 | Takahashi | A61B 6/032 |
| 2018/0252657 A1* | 9/2018 | Persson | A61B 6/482 |

OTHER PUBLICATIONS

Shin-ichiro Iwamoto, et al., "Correction Method of Nonlinearity Due to Logarithm Operation for X-Ray CT Projection Data with Noise in Photon-Starved State", IEICE Trans. Inf. & Syst., vol. E90-D, No. 10, Oct. 2007, pp. 1697-1705.

Jean-Baptiste Thibault, et al., "A Recursive Filter for Noise Reduction in Statistical Iterative Tomographic Imaging", SPIE Proceedings Computational Imaging IV, vol. 6065, Feb. 2, 2006, 10 pages.

Shin-ichiro Iwamoto, et al., "Statistical Influence of Logarithmic Transform of Projection Data with Noise and a Simple Correction Method", Med Imag Tech, vol. 24, No. 3, May 2006, pp. 209-215 (with English Abstract).

Patrick J. La Rivière, et al., "Penalized-Likelihood Sinogram Restoration for Computed Tomography", IEEE Transactions on Medical Imaging, vol. 25, No. 8, Aug. 2006, pp. 1022-1036.

Jiang Hsueg, "Adaptive streak artifact reduction in computed tomography resulting from excessive x-ray photon noise", Medical Physics, vol. 25, No. 11, Nov. 1998, pp. 2139-2147.

Lin Fu, et al., "Comparison between Pre-log and Post-log Statistical Models in Low-Dose CT Iterative Reconstruction", IEEE Medical Imaging Conference, 2014, 10 pages.

Zhi Yang, et al., "Effective Data-domain Noise and Streak Reduction for X-Ray CT", Radiology and Nuclear Medicine. vol. 44, Issue 37, 2011, 1 page.

Issei Mori, et al., "Method for Suppressing Streak Artifacts in CT Resulting from Excessive Noise", Med Imag Tech, vol. 21, No. 4, Sep. 2003, pp. 272-276 (with English Abstract).

* cited by examiner

… (1)

APPARATUS AND METHOD FOR CORRECTING BIAS IN LOW-COUNT COMPUTED TOMOGRAPHY PROJECTION DATA

FIELD

This disclosure relates to bias correction of data undergoing a positivity mapping image reconstruction using computed-tomography (CT) projection data, and, more particularly, to bias correction for low-count computed-tomography (CT) projection data undergoing a positivity mapping and a logarithm operation prior to image reconstruction.

BACKGROUND

Computed tomography (CT) systems and methods are widely used, particularly for medical imaging and diagnosis. CT systems generally create images of one or more sectional slices through a subject's body. A radiation source, such as an X-ray source, irradiates the body from one side. At least one detector on the opposite side of the body receives radiation transmitted through the body. The attenuation of the radiation that has passed through the body is measured by processing electrical signals received from the detector.

A CT sinogram indicates attenuation through the body as a function of position along a detector array and as a function of the projection angle between the X-ray source and the detector array for various projection measurements. In a sinogram, the spatial dimensions refer to the position along the array of X-ray detectors. The time/angle dimension refers to the projection angle of X-rays, which changes as a function of time during a CT scan. The attenuation resulting from a portion of the imaged object (e.g., a vertebra) will trace out a sine wave around the vertical axis. Those portions farther from the axis of rotation correspond to sine waves with larger amplitudes, and the phase of the sine waves correspond to the angular positions of objects around the rotation axis. Performing an inverse Radon transform—or any other image reconstruction method—reconstructs an image from the projection data in the sinogram.

X-ray CT has found extensive clinical applications in cancer, heart, and brain imaging. As CT has been increasingly used for a variety of applications including, e.g., cancer screening and pediatric imaging, there has arisen a push to reduce the radiation dose of clinical CT scans to become as low as reasonably achievable. However, one challenge of reducing the radiation dose is that, as the measured intensity approaches the baseline level, noise can be on the same order of magnitude as the signal. When this occurs, baseline subtraction can result in the signal sometime being negative. These negative values create problems when the logarithm is taken of these negative values. The logarithm operation is used to convert intensity values to attenuation values by taking the logarithm of the measured intensity normalized to a calibration scan in the absence of absorptive material in the imaging volume. Various techniques can be used to correct for negative intensity values, but these corrections introduce a bias to the data, resulting in bias artifacts. Current methods for positivity mapping to correct for negative intensity values do not accurately minimize this bias.

BRIEF DESCRIPTION OF THE DRAWINGS

A more complete understanding of this disclosure is provided by reference to the following detailed description when considered in connection with the accompanying drawings, wherein.

DETAILED DESCRIPTION

Figure 1A:
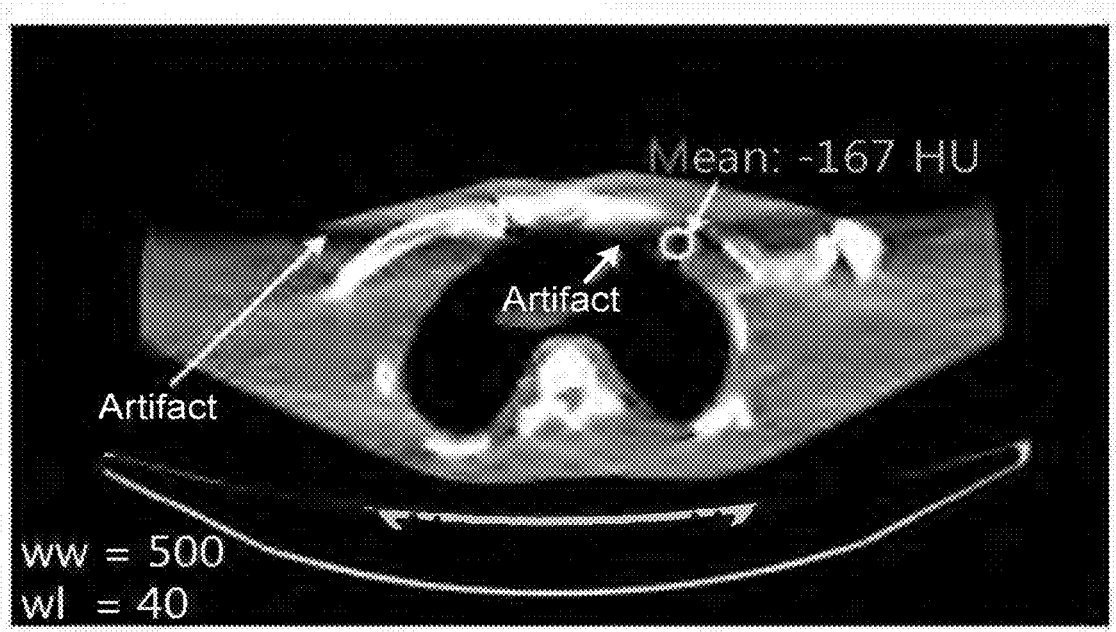
FIG. 1A shows a reconstructed image of a shoulder phantom from generated using a CT scan with an X-ray tube current of 5 mAs and a voltage of 120 kVp.

In general, it is desirable to reduce CT radiation dose as low as reasonably achievable (ALARA) while maintaining diagnostic quality. Clinical applications for which reduced radiation dose and low-count computed tomography (CT) are advantageous include: CT perfusion study, low and ultra-low-dose CT screening, low dose whole body imaging for melanoma or pediatrics, bias/noise reduction for lower kVp imaging in dual energy CT to reduce total dose, ultra-low-dose CT for PET/CT attenuation correction (CTAC), respiratory-gated CT for phased matched CTAC, and motion correction for PET. However, at very low count levels, non-positive measurements occur, which presents a challenge when the data is converted using a logarithmic operation. Positive mapping can be applied to handle non-positive counts by mapping non-positive counts to positive values, but the positivity maps can have the drawback of introducing bias. In turn, this bias can result in artifacts for reconstructed images generated from the CT projection data. Further, according to Jenson's inequality, the application of the logarithmic operation to the data can also introduce a statistical bias because the logarithmic operation is a nonlinear operation on the noise distribution, such that the logarithm of the mean of the statistical distribution representing the noise is different from the mean of the logarithm of the statistical distribution representing the noise.

Accordingly, the methods and apparatus described herein can overcome the above-identified post-log bias in the projection data and artifacts in the reconstructed image that result from this bias. The methods described herein generate a lookup table to determine and correct the post-log bias based on a pre-log mean estimate of the projection data.

In certain implementations of the methods described herein, the mean value is estimated from the pre-log data. This pre-log data is then mapped to positive numbers and the logarithm is then taken to generate post-log data. Next, using a look-up table, the estimated mean value of the pre-log data is used to determine, on a pixel-by-pixel basis, the bias of the post-log data, and this estimated bias is subtracted pixel-by-pixel from the post-log data. Accordingly, the bias can accurately be accounted for and corrected, and artifacts associated with the bias can be mitigated.

After, the post-log data has been bias corrected, other corrections can also be performed on the data, including, for example, a beam-hardening correction. At this point, a CT image can be reconstruction from the projection data. Any known method of image reconstruction can be used, including: statistical iterative reconstruction (IR), filtered back-projection (FBP), or any other known method. Additional, image reconstruction steps, such as material decomposition, can also be performed, either before or after the CT image is reconstructed.

For example, a post-log iterative reconstruction (IR) method has certain benefits and challenges. For instance, IR methods performed in the post-log domain can have fast convergence, but, without bias correction, the resulting image quality may be suboptimal for low-count CT data due to the log calculation. In the post-log method, the logarithm of a ratio is calculated, the ratio being between a blank scan (e.g., using an empty CT scanner) and a raw scan (e.g., with an object OBJ that is to be imaged). The result is post-log sinogram data representing line integrals (i.e., projections) of the X-ray attenuation through the object OBJ. IR methods, such as the IR filtered back-projection (FBP) reconstruction or the penalized weighted least squares (PWLS) method, can then be used to reconstruct the CT image from the sinogram data (i.e., the projection data arranged in sequence by projection angle).

As mentioned above, the log calculation can be sensitive to noise and can amplify measurement noise when the dose is low and is undefined for negative measurements. Because the logarithm of a negative number is undefined, the baseline subtraction from low-dose measurements can be corrected using a positivity mapping, which transforms negative values to positive values. The positivity mapping can be as simple as taking the absolute value of the measured X-ray intensity after a baseline subtraction. Regardless of which positivity mapping is used, a bias will be introduced and this bias can result in artifacts in the reconstructed image.

The statistical processes in CT imaging are generally complicated and can be modeled using compound Poisson distributions. After preprocessing the X-ray detector counts to account for calibrations and data corrections (e.g., beam-hardening, detector nonlinearities, k escape, pileup, etc.), CT data can, in practice, be modeled by independent random variables following a Poisson (or compound Poisson) distribution, to represent the statistical distribution of the X-ray signal, plus a Gaussian distribution, to account for electronic noise in the measurement. The statistical model of the random variable $Y_i$ measured by the detector element i can be described as $$Y_i \sim \text{Poisson}(\bar{y}_i(x)) + \text{Gaussian}(0, \sigma_\epsilon^2) \qquad \text{Eq. (1)}$$

wherein $\sigma_\epsilon^2$ denotes the standard deviation of electronic noise. The value $\bar{y}_i(x)$ is the expected projection data related to the image of linear material attenuation coefficient x by means of a nonlinear transformation, which is given by $$\bar{y}_i(x) = b_i \exp(-[Ax]_i) + r_i \qquad \text{Eq. (2)}$$

wherein $b_i$ is the measurement in the detector element i by the blank scan, and $r_i$ is the mean of background measurement (e.g., scattered photons). The (i; j)th element of the system matrix A represents the line integral of attenuation for X-ray photons passing through the image pixel j and being detected by the detector element/pixel i.

Inclusion of the electronic noise modeling can improve low-dose CT image reconstruction. However, there is no simple analytical form for the likelihood function of the combined Poisson and Gaussian model in Eq. (1), and, therefore, use of this model can be computationally challenging. Another statistical model is the shifted-Poisson model $$\hat{Y}_i = [Y_i + \Sigma_\epsilon^2]_+ \sim \text{Poisson}(\bar{y}_i(x) + \sigma_\epsilon^2), \quad \text{Eq. (3)}$$

wherein $[\bullet]_+$ is threshold function that sets negative values to zero. The first two orders of statistical moments (mean and variance) of the shifted-Poisson model can be matched with that of the Poisson-Gaussian model. The shifted-Poisson model is more attractive in practice than other more complex models because it makes computation more tractable.

The realizations of random variable Y in all detector elements can be denoted by $y \in \mathbb{R}^{n_i \times 1}$, wherein $n_i$ is the number of detector elements. The pre-log methods can reconstruct the attenuation image x either from the measurement y using a complex likelihood function or from the shifted data $$\hat{Y}_i = [Y_i + \sigma_\epsilon^2]_+ \sim \text{Poisson}(\bar{y}_i(x) + \sigma_\epsilon^2), \quad \text{Eq. (4)}$$

using the tractable shifted-Poisson model. In addition to the shifted-Poisson model and the Poisson-Gaussian model, the statistical model can be a Poisson model, a compound Poisson model, or any other statistical distribution or combination of statistical distribution representing the noise in the system.

For the shifted-Poisson model, the image estimate is obtained by maximizing the log likelihood function of the shifted-Poisson model, which is given by $$\hat{x} = \arg\max_{x \geq 0} \sum_i [\hat{y}_i \log(\bar{y}_i(x) + \sigma_\epsilon^2) - (\bar{y}_i(x) + \sigma_\epsilon^2)] - \beta U(x), \quad \text{Eq. (5)}$$

wherein $U(x)$ is an image roughness penalty and $\beta$ controls the strength of the regularization. The regularization term $U(x)$ can be determined as the intensity difference between neighboring pixels, which is given by $$U(x) = \sum_j \sum_{k \in \aleph_j} w_{jk} \psi_\delta(x_j - x_k), \quad \text{Eq. (6)}$$

wherein $\psi_\delta(t)$ is the penalty function, $\delta$ is a parameter that controls the smoothness of the penalty function, $w_{jk}$ is the weighting factor related to the distance between pixel j and pixel k in the neighborhood $\aleph_j$. An example of $\psi_\delta(t)$ is the Huber function, which can be expressed as $$\psi_\delta(t) = \begin{cases} \frac{1}{2}t^2, & \delta \geq |t| \\ \delta|t| - \frac{\delta^2}{2}, & \text{otherwise.} \end{cases} \quad \text{Eq. (7)}$$

In addition to the Huber function, the regularization term $U(x)$ can be a quadratic regularization term, a total variation minimization term, or any other regularization term.

In certain implementations, the above optimization problem expressed in Eq. (5) can be solved by the separable paraboloidal surrogate (SPS) approach with acceleration by ordered subsets (OS), for example. In general any optimization method can be used to solve Eq. (5), including, for example, a gradient-descent method or other known methods. Further examples of optimization methods that can be used to solve the above optimization problem expressed in Eq. (5) include: an augmented-Lagrangian method, an alternating direction-method-of-multiplier method, a Nesterov method, a preconditioned-gradient-descent method, an ordered subset method, or a combination of the foregoing.

The post-log IR methods employ a log calculation to remove the nonlinearity in Eq. (2) and simplify the reconstruction problem. In certain implementations, the line integral of the attenuation for each detector element i can be calculated from the measurement $y_i$ by $$\hat{l}_i = \log \frac{b_i}{y_i - r_i}. \quad \text{Eq. (8)}$$

The expected data of the post-log sinogram $\hat{l}$ scan be linearly related to the image to be reconstructed, such that the relation between the post-log sinogram and the reconstructed image x is given by the system-matrix equation $$\bar{l}(x) = Ax. \quad \text{Eq. (9)}$$

In certain implementations, the image x can be reconstructed from $\hat{l}$ using the penalized weighted least squares (PWLS) formulation, which is given by the expression $$\hat{x} = \arg\min_{x \geq 0} \sum_i \frac{w_i}{2} (\hat{l}_i - \bar{l}_i(x))^2 + \beta U(x), \quad \text{Eq. (10)}$$

wherein the weighting factor $\{w_i\}$ can represent an approximate inverse variance of $\hat{l}$ that is derived from the Poisson model, $$w_i = \frac{y_i^2}{y_i + \sigma_\epsilon^2} \quad \text{Eq. (11)}$$

The post-log reconstruction problem in Eq. (10) can be solved using any known optimization method such as the OS-SPS algorithm and any of the optimization methods discussed above, for example. The convergence of the optimization method operating on Eq. (10) is usually fast.

The post-log data can be used to reconstruct a CT image using an IR method as described above. Alternatively, the post-log data can be used to reconstruct a CT image using filtered back-projection method.

Figure 1B:
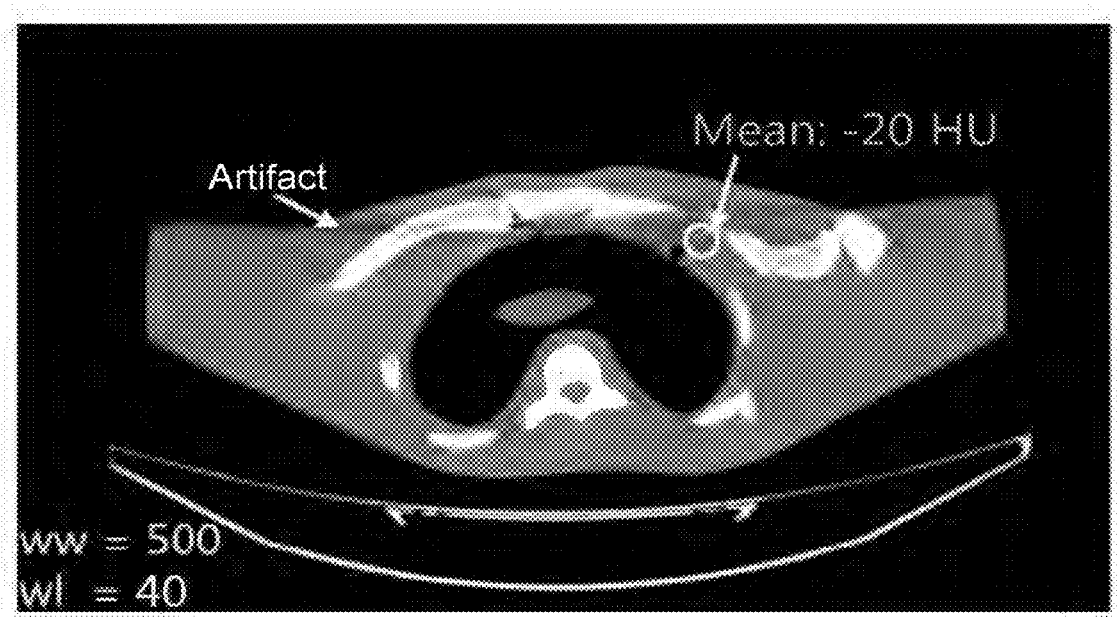
FIG. 1B shows a reconstructed image of a shoulder phantom from generated using a CT scan with an X-ray tube current of 100 mAs and a voltage of 120 kVp.

Referring now to the drawings, wherein like reference numerals designate identical or corresponding parts throughout the several views, FIGS. 1A and 1B show plots of reconstructed CT images of a shoulder phantom using FBP and using different exposures. FIG. 1A was obtained using an X-ray tube set to a voltage of 120 kVp and a current of 5 mAs, whereas FIG. 1B was obtained using an X-ray tube set to a voltage of 120 kVp and a current of 100 mAs. Comparing with FIG. 1B, FIG. 1A shows severe dark-band artifact which is due to photon-starvation at lower exposure level. For example, a mean value was taken over similar regions within the artifact (shown by the white circle). In FIG. 1A the mean value was −167 Hounsfield units (HU), and in FIG. 1B the mean value for a similar region was −20 HU. Both of the reconstructed images in FIGS. 1A and 1B use data that was corrected for non-positive values before taking the logarithm, but, for both FIGS. 1A and 1B, a bias correction was not performed. As a result, without bias correction, the X-ray attenuation, especially for low-count pixels of the projection data, is biased to underestimate the attenuation, resulting is a bias drift at low-count levels. This biased drift at low-count levels generates the dark/white band and streak artifacts observed in the reconstructed image shown in FIG. 1A, for which the counts are especially low.

The bias can be decreased in several ways. For example, the projection data can be transformed/mapped using the tangent of the logarithmic curve instead of by the logarithmic curve when the number of captured photons is below a certain threshold, which is referred to as a "log-tweak," i.e., the logarithm function is tweaked slightly. However, at extremely low-count levels, this transformation/mapping can be ineffective to correct for bias, and can introduce other artifacts particular associated with this tangent-of-the-logarithmic-curve transformation.

Alternatively, sinogram denoising/smoothing can also be used to reduce CT noise and artifacts because the decreased noise indirectly reduces CT bias at low counts. However, this approach can only help so much because it focuses on only noise reduction, rather than bias correction. Some residual noise will still be present, and this residual noise, when corrected for non-positive values, can still result in a bias and corresponding artifacts in the reconstructed image. In addition, sinogram smoothing introduces correlation between different channels, and can degrade spatial resolution, especially at low-count levels.

Further, the bias can be decreased using analytical methods to correct for the nonlinearity of the logarithm by making the assumption that the measurements are Gaussian distributed. However, at low-count levels, the measurements are not Gaussian distributed, making these methods ineffective for low-count data.

In certain implementations, the bias problem can be obviated by using an IR method that includes pre-log model-based, as opposed to a post-log model. Unfortunately, pre-log IR methods typically have a slow convergence speed due to the nonlinearities in the pre-log IR and also due to the use of exponential operators during the pre-log IR method, resulting in significantly longer reconstruction times.

All of the above challenges can be overcome by using the methods described herein, which corrects for the bias introduced by the logarithmic transformation and by the positivity mappings. The methods described herein include a general framework for post-log data bias correction preparing the data for CT reconstruction. These methods can include a bias correction look-up-table (LUT), which can be generated using any positivity mapping functions at any count level. Further, the LUT can be generated using either calculated data derived using a statistical model of the X-ray detection process or actual measurements, which incorporate the physical effects of the X-ray detection, including the polychromatic spectrum, a range of X-ray fluxes, and a range of X-ray tube settings (e.g., voltages and currents).

Figure 2:
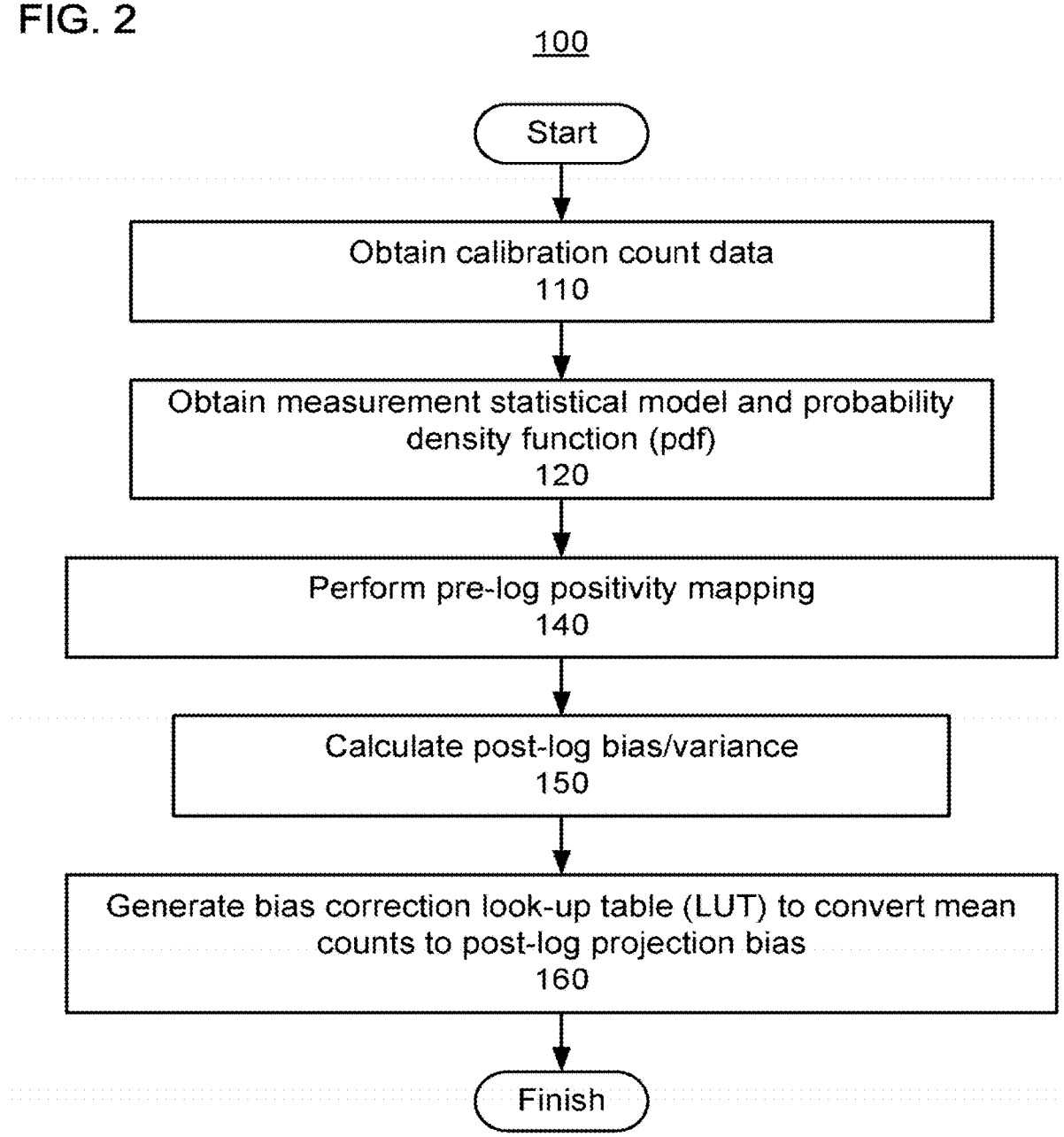
FIG. 2 shows a flow diagram of a method for generating a bias-correction look-up table, according to one implementation.

FIG. 2 shows method 100 for generating the LUT.

In step 110 of method 100, calibration data is obtained, representing a count or intensity measurement of X-rays at respective detector elements of an X-ray detector array of a CT scanner. As discussed above, the calibration data can be either calculated from a statistical model or can be measured empirically using the X-ray source and detectors of a CT scanner, such as the CT scanner described herein or any other CT scanner.

In step 120 of method 100, the statistical model is obtained to generate a probability density function (PDF). For example, the statistical model can be any known model for the detection of radiation using a noisy detector, including those models described above. In this section, a compound Poisson plus Gaussian model is assumed. The PDF can be obtained by retrieving it from a computer-readable memory or by deriving it from empirical data. Each element of the detector array can have a unique probability density function.

First, the generation of the LUT using calculated data is described. Next, the generation of the LUT using empirical measurements is described.

For calculated data, a compound Poisson-plus-Gaussian noise model is a reasonable model to approximate measurements for energy-integrated X-ray CT, for example. The actual analytical form of the PDF can be complicated, and other models are possible. In certain implementations, a numerical FFT-based method can be applied to calculate the approximate PDF. The compound Poisson noise can be calculated by, first, taking a fast Fourier transform (FFT) of an incident X-ray spectrum $\phi(X)$, to generate $\varphi_X(t)$. Then the PDF $f_S(x)$ of Compound Poisson Quantum Noise S can be calculated by taking the inverse FFT of the function $$\varphi_S(t)=\exp(\lambda(\varphi_X(t)-1)), \quad \text{Eq. (12)}$$

wherein $\lambda$ is the mean photon count. Next, the electronic noise can be modeled as being zero mean (after dark-current subtraction) with a variance of $\sigma$, and the Gaussian PDF of the electronic noise can be given by $$f_N(x) = \frac{1}{\sigma\sqrt{2\pi}}\exp\left(-\frac{x^2}{2\sigma^2}\right). \quad \text{Eq. (13)}$$

Finally, the PDF for the entire measurement including both the noise from the X-rays and the electronic noise from the detectors can be calculated as the convolution between the Compound Poisson and Gaussian PDFs above, i.e., $$f_{Total}(x)=f_S(x)*f_N(x), \quad \text{Eq. (14)}$$

wherein '*' represents the convolution operator.

To generate a measurement-based PDF, the process is to first select a scan condition by choosing settings for the X-ray source (e.g., by choosing select values for the setting of the voltage and current of the X-ray source to obtain different mean count rates). Next, a data set can be generated by applying repeated scans on a specific phantom (e.g., water phantom). Then, the data from the same detector element over repeated scans can be treated as independent random variables, and an empirically derived PDF can be generated for each detector element.

In step 140 of method 100, a positivity mapping can be applied to the calibration data. This mapping transforms non-positive values to positive values. Any known positivity mapping can be applied. For example, positivity mapping functions PM(x) can use a threshold method (e.g., PM(x)=max(x, ε), wherein ε is a pre-defined small positive number), an absolute-value method (e.g., PM(x)=|x|), an exponential shift curve (ESC) (e.g., PM(x)=α log(exp(x/α+1))), and a log-tweak method. Additionally, the positivity mapping functions PM(x) can be performed using a Maximum-likelihood mapping PM(x)=L(x), wherein L(x) is the generated LUT based on a maximum likelihood estimation.

In step 150 of method 100, after the pre-log-positivity mapping a logarithm is taken of the calibration data to generate the post-log calibration data. Then the bias and variance of post-log calibration data are calculated relative to ground truth values $\Theta_{true}$. The ground truth values are known values for the data in the absence of noise. For example, for the measured calibration data, the ground truth can be obtained by averaging a large data set for each pixel prior to taking the logarithm, or by using known values for the X-ray signal in the absence of the phantom and the known attenuation of the phantom. For the calculated calibration data the ground truth can be calculated directly. The post-log ground truth values $\Theta_{true}$ can be calculated from the pre-log ground truth values $X_{true}$ by applying the expression $$\Theta_{true} = \log(X_{true}).\qquad\text{Eq. (15)}$$

Note, the positivity mapping is not applied to the ground truth values. The post-log calibration data is generated using the expression $$\hat{\Theta} = \log(PM(x)).\qquad\text{Eq. (16)}$$

The bias $\text{Bias}_\Theta$ is then calculated as $$\text{Bias}_\Theta = E(\hat{\Theta}) - \Theta_{true},\qquad\text{Eq. (17)}$$

wherein $E(\cdot)$ is an expectation value operator. When the theoretical PDF $f_{Total}(X)$ is known, e.g., when using calculated calibration data, a numerical integral can be applied to get the expectation value directly from the PDF, as given by the expression $$E(\hat{\Theta}) = \int_{-\infty}^{\infty} \log(PM(x)) f_{Total}(x) dx.\qquad\text{Eq. (18)}$$

Thus, it is sufficient to know the theoretical PDF, without actually simulating particular values derived using the PDF. That is, when a PDF is assumed step 110 can be omitted. For measurement-based calibration data, expectation values can be calculated based on the empirically derived data set.

In step 160 of method 100, a LUT is constructed in post-log domain to relate the pre-log true values $X_{true}$ to the post-log bias represented by the expectation value for noisy data after the positivity mapping and logarithm operations. Thus, each pre-log true value $X_{true}$ within a predefined range will have a corresponding bias value $\text{Bias}_\Theta$. Further, because only a discrete number of values can be stored, extrapolation can be used to determine the bias value $\text{Bias}_\Theta$ corresponding to a true value $X_{true}$ in between those discrete value recorded in the LUT.

Similarly, the variance after bias correction can also be calculated based on the PDF, and this variance can be included in statistically iterative reconstruction for calculating the statistical weights $w_i$, which are given in Eq. (11).

Figure 3:
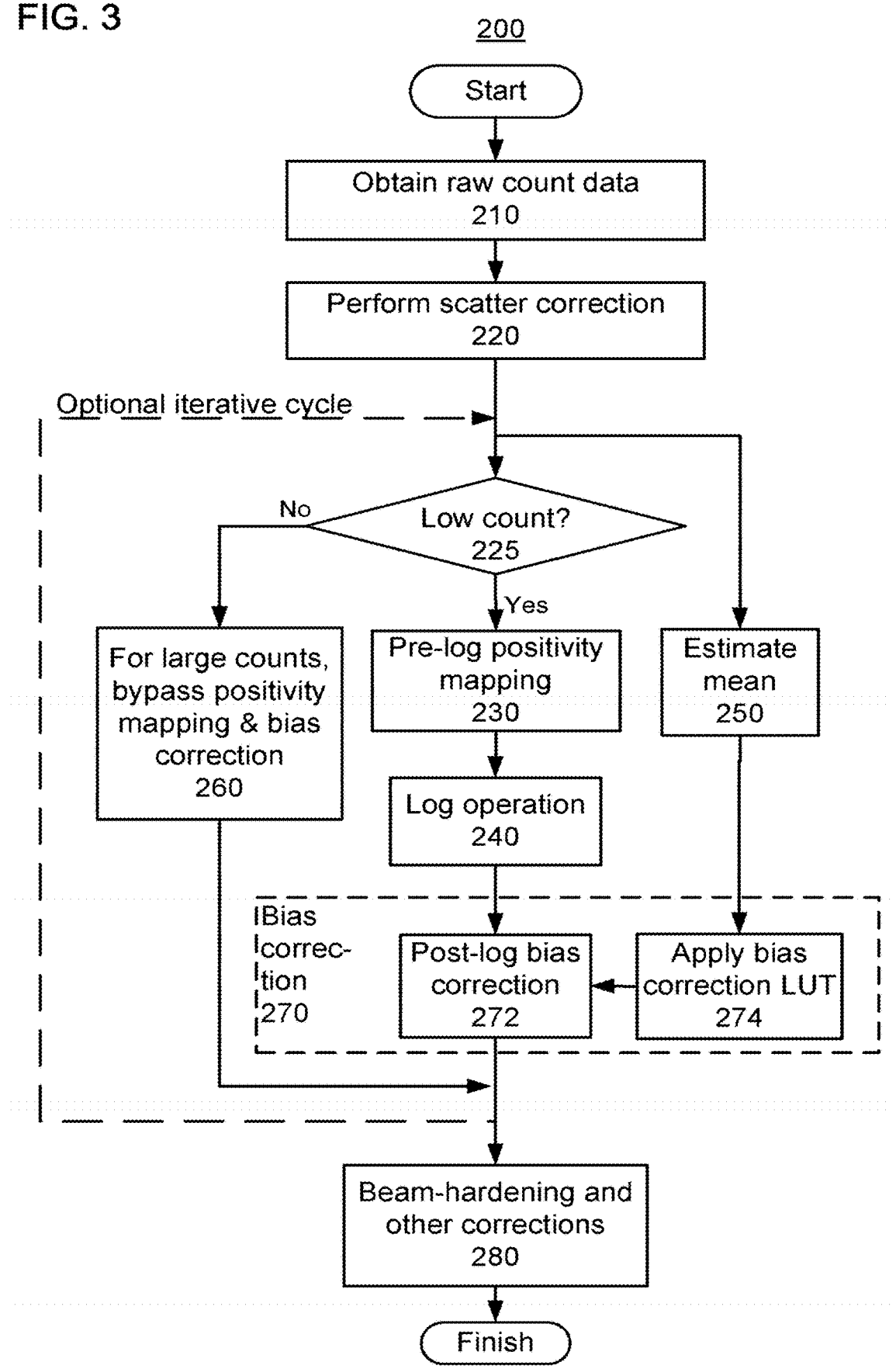
FIG. 3 shows a flow diagram of a method of performing bias correction using a bias-correction look-up table, according to one implementation.

FIG. 3 shows a flow chart of a method 200 of performing bias correction with reference to the bias-correction LUT.

In step 210 of method 200, raw count data is obtained. The raw count data can be measured using a CT scanner, such as the CT scanner described herein.

In step 220 of method 200, scatter correction and/or other data conditioning and preprocessing can be performed. Any known scatter correction method can be used, including a kernel-based scatter-correction method, Monte-Carlo scatter-correction method, and radiative-transfer-equation scatter-correction method.

In step 225 of method 200, an inquiry is performed for each pixel of each detector element, regarding whether the registered count is a low count below a predefined threshold or a high count exceeding the predefined threshold. When the count is low, the positivity mapping and bias correction steps are performed by proceeding from step 225 to step 230. Otherwise, the positivity mapping and bias correction are bypassed, and method 200 proceeds from step 225 to step 260.

In step 230 of method 200, a pre-log positivity mapping PM(x) of the pre-log data is performed. This pre-log positivity mapping PM(x) is the same pre-log positivity mapping used when generating the bias-correction LUT. In certain implementations, a user can select among various pre-log positivity mappings PM(x), each corresponding to its respective bias-correction LUTs, and the corresponding bias-correction LUTs will be used to determine the bias correction in step 274 of method 200.

In step 240 of method 200, the logarithm operation is performed on the pre-log data after the positivity mappings.

In step 250 of method 200, the pre-log data is used to estimate a mean value for each pixel of each detector element. For example, to reduce noise, a spatial filtering and/or denoising process can be performed on the pre-log projection images (i.e., the pre-log data). Any known method can be used to denoise the data and to estimate the mean values for each pixel. For example, the mean can be estimated using a simple Gaussian estimator, or a sophisticated count adaptive mean estimator, such as a count adaptive Gaussian estimator or a local linear minimum mean squared error (LLMMSE) filter. Additionally, model-based sinogram restoration methods can be used to estimate mean counts of the noisy measurements after the scatter correction. Further, in step 250 of method 200, various denoising methods can be applied to the respective scatter corrected projection images of the pre-log data. These various denoising methods can include linear smoothing filters, anisotropic diffusion, non-local means, and nonlinear filters.

Linear smoothing filters remove noise by convolving the original image with a mask that represents a low-pass filter or smoothing operation. For example, the Gaussian mask comprises elements determined by a Gaussian function. This convolution brings the value of each pixel into closer agreement with the values of its neighbors. In general, a smoothing filter sets each pixel to the average value, or a weighted average, of itself and its nearby neighbors; the Gaussian filter is just one possible set of weights. Disadvantageously, smoothing filters tend to blur an image because pixel intensity values that are significantly higher or lower than the surrounding neighborhood are smeared or averaged across their neighboring area. Sharp boundaries become fuzzy. Generally, local linear filter methods assume that local neighbourhood are homogeneous, and local linear filter methods, therefore, tend to impose homogeneity on the image obscuring non-homogeneous features, such as lesions or organ boundaries.

Anisotropic diffusion removes noise while preserving sharp edges by evolving an image under a smoothing partial differential equation similar to the heat equation. If the diffusion coefficient were spatially constant, this smoothing would be equivalent to linear Gaussian filtering, but when the diffusion coefficient is anisotropic according to the presence of edges, the noise can be removed without blurring the edges of the image.

A median filter is an example of a nonlinear filter and, if properly designed, a nonlinear filter can also preserve edges and avoid blurring. A median filter operates, for example, by evaluating each pixel in the image, sorting the neighboring pixels according to intensity, and replacing the original value of the pixel with the median value from the ordered list of intensities. The median filter is one example of a rank-conditioned rank-selection (RCRS) filter. For example, median filters and other RCRS filters can be applied to remove salt and pepper noise from an image without introducing significant blurring artifacts.

In addition a filter using a total-variation (TV) minimization regularization term can be used where it is assumed that the areas being imaged are uniform over discrete areas with relatively sharp boundaries between the areas. A TV filter can also be used as another example of a nonlinear filter.

In non-local means filtering, rather than performing a weighted average of pixels according to their spatial proximity, pixels are determined to be a weighted average according to the similarity between patches within the images. Thus, noise is removed based on non-local averaging of all the pixels in an image not just the neighboring pixels. In particular, the amount of weighting for a pixel is based on the degree of similarity between a small patch centered near that pixel and another small patch centered on the pixel being denoised.

In step 270 of method 200, the bias correction is performed on the post-log data, using the estimated means from the pre-log data.

In step 274 of method 200, a bias correction value is determined by using the bias-correction LUT to find the bias value corresponding to the estimated mean for a given pixel value of the post-log projection data.

In step 272 of method 200, the post-log projection data is corrected by subtracting off the bias value determined in step 274.

In step 260 of method 200, the logarithm operation is applied to those counts that are determined to be above the predefined threshold. These high-count data do not undergo the operations of positivity mapping and bias correction.

In step 280 of method 200, beam-hardening corrections and other corrections can be performed on the bias-corrected post-log data. After these additional corrections are performed the data can be used to reconstruct a CT image. Any known CT reconstruction methods can be used.

In certain implementations, the post-log bias corrected data obtained from step 272 can by cycled back to steps 225 and 250 by taking an exponential of each of the post-log values and then using the exponential of the bias-corrected post-log data as a primary component from the scatter correction. Thus, each of steps 225, 230, 240, 250, 260 and 270 can be repeated to further refine the low-count data by preforming the operations of the positivity mapping and the bias correction. This cycle of performing steps 225, 230, 240, 250, 260 and 270 and then taking the exponential of the result to start the cycle again can be performed as many times as needed to refine the low-count data.

By correcting for the bias introduced by the positivity mapping and the logarithm operation, the methods described herein offer several advantages over previous methods. The methods described herein provide a new framework for correcting for low-count bias in CT. This method is effective for low-count bias correction, independent of the CT image reconstruction method (e.g., IR or FBP). Further, the methods described herein are flexible, and can be used for any positivity mapping functions. Moreover, these methods are easy and straightforward to implement, with little additional computational overhead and additional computational resources. Additionally, unlike sinogram smoothing based methods, the methods described herein avoid creating noise correlation between different channels for low-count levels.

Figure 4A:
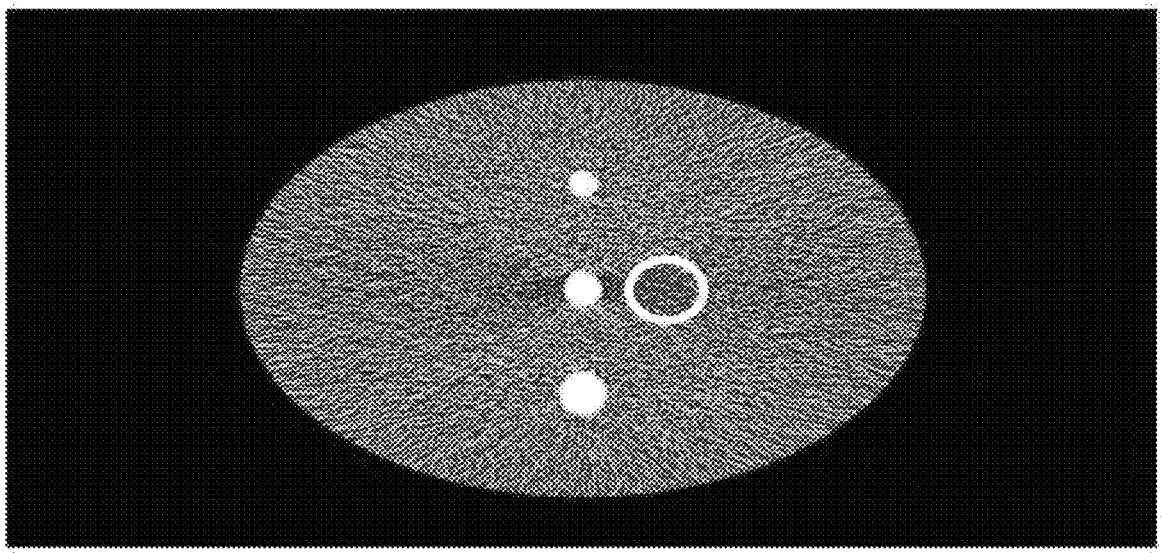
FIG. 4A shows a reconstructed image of a water phantom with bone inserts using a log-tweak positivity mapping, wherein the data is acquired using an X-ray tube current of 50 mAs.
Figure 4B:
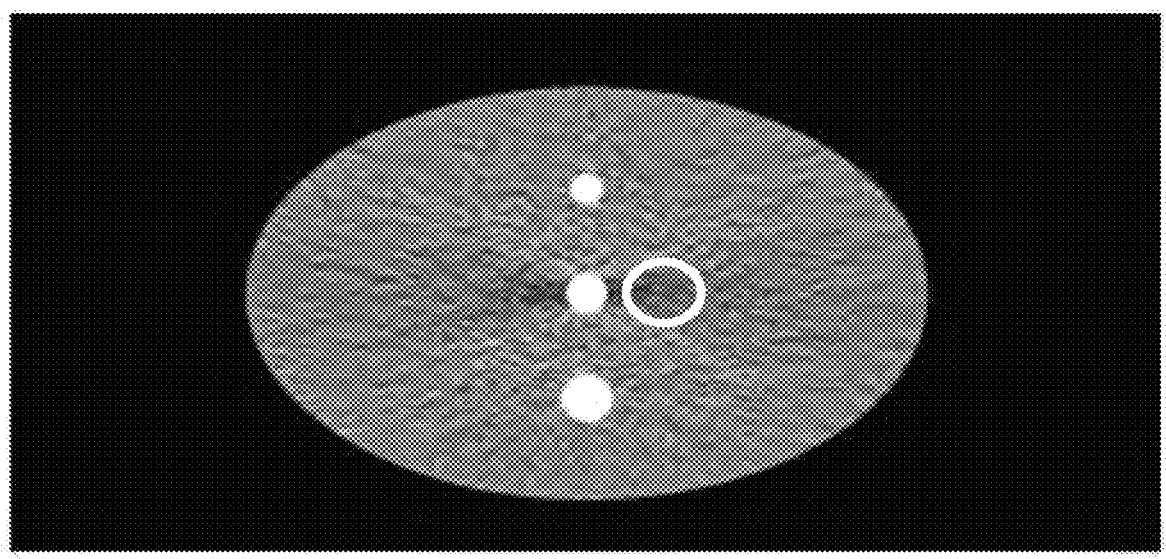
FIG. 4B shows a reconstructed image of a water phantom with bone inserts using sinogram smoothing and a log-tweak positivity mapping, wherein the data is acquired using an X-ray tube current of 50 mAs.
Figure 4C:
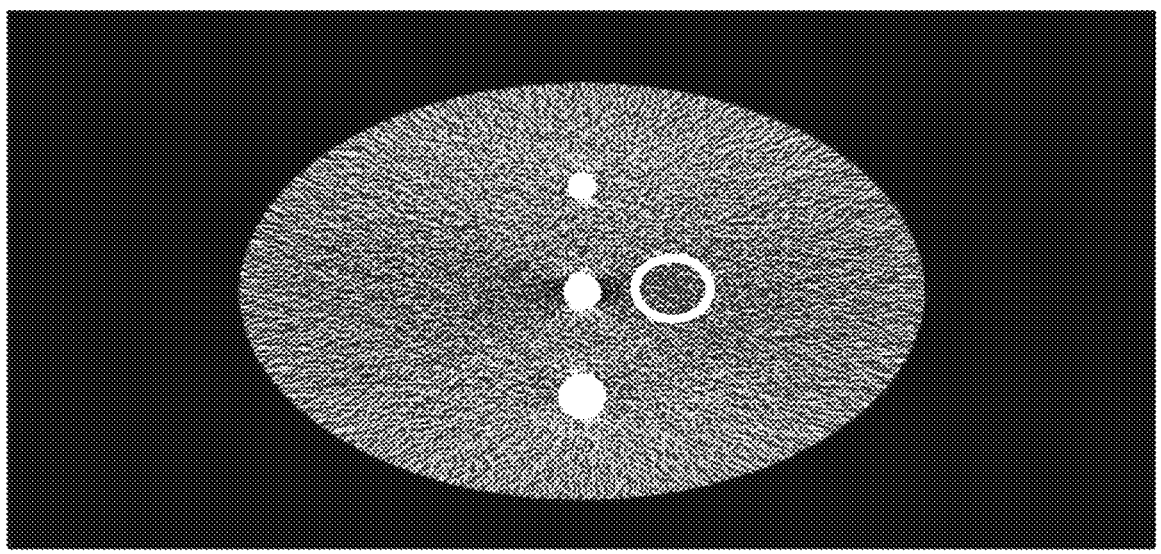
FIG. 4C shows a reconstructed image of a water phantom with bone inserts using an exponential shift curve (ESC) positivity mapping with a value of $\alpha=10$ and without bias correction, wherein the data is acquired using an X-ray tube current of 50 mAs.
Figure 4D:
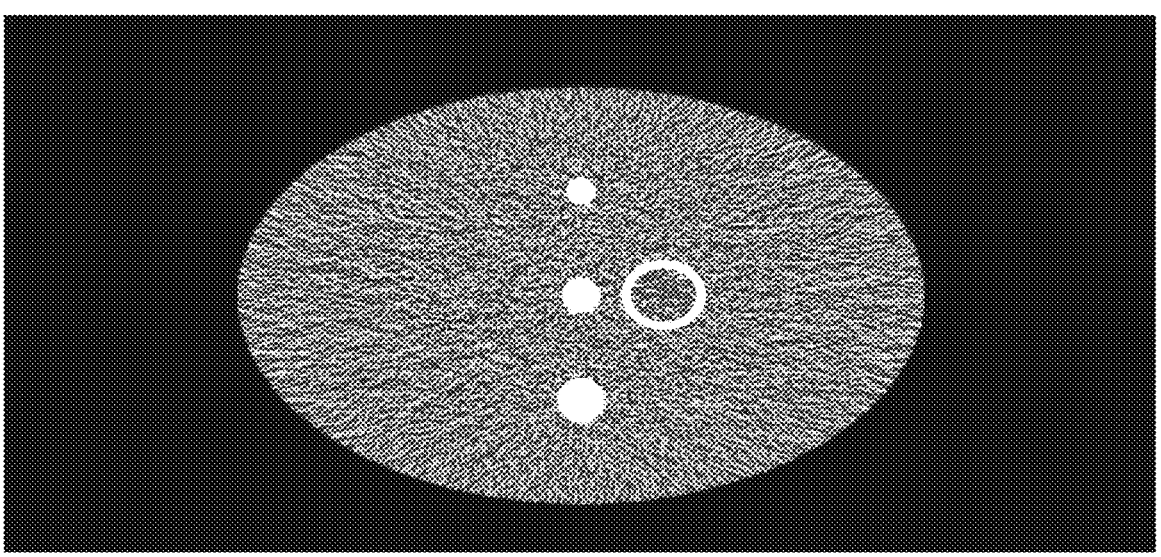
FIG. 4D shows a reconstructed image of a water phantom with bone inserts using an ESC positivity mapping with a value of $\alpha=10$ and with bias correction, wherein the data is acquired using an X-ray tube current of 50 mAs.
Figure 4E:
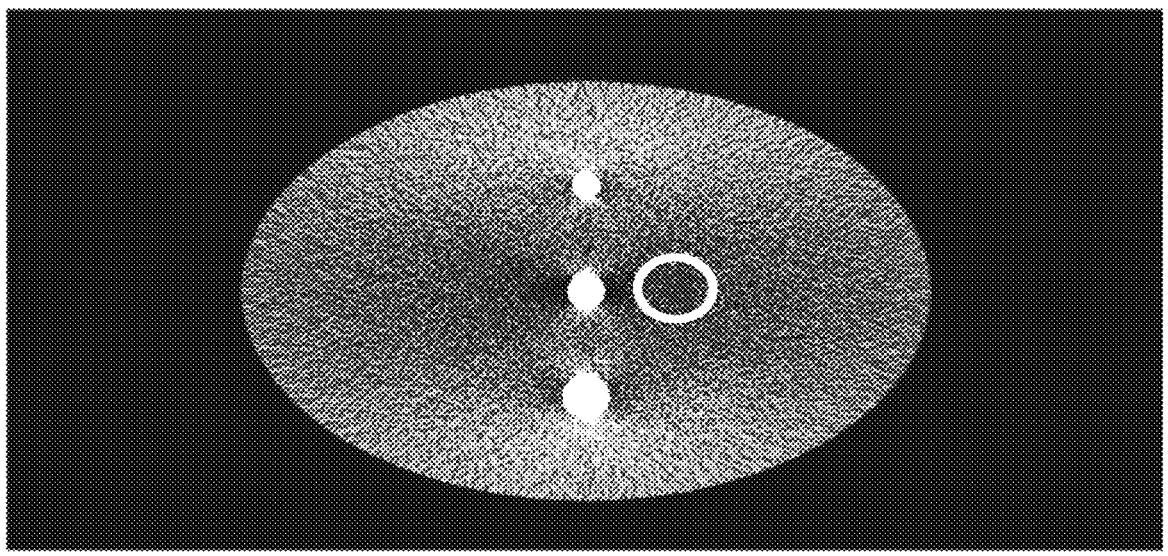
FIG. 4E shows a reconstructed image of a water phantom with bone inserts using an ESC positivity mapping with a value of $\alpha=20$ and without bias correction, wherein the data is acquired using an X-ray tube current of 50 mAs.
Figure 4F:
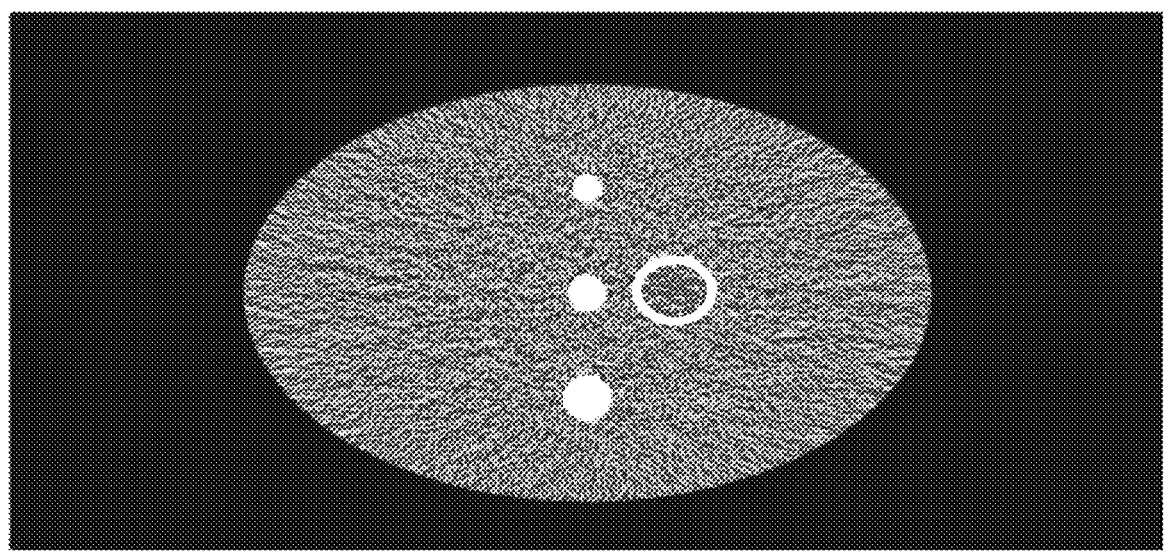
FIG. 4F shows a reconstructed image of a water phantom with bone inserts using an ESC positivity mapping with a value of $\alpha=20$ and with bias correction, wherein the data is acquired using an X-ray tube current of 50 mAs.

FIGS. 4A, 4B, 4C, 4D, 4E, and 4F show reconstructed images generated from projection data acquired using a water phantom with bone inserts. The voltage across the X-ray tube is 80 kVp and the current was 50 mAs. FIG. 4A shows a reconstructed image using a log-tweak positivity mapping without bias correction. FIG. 4B shows a reconstructed image using sinogram denoising/smoothing together with a log-tweak positivity mapping without bias correction. FIG. 4C shows a reconstructed image using an exponential shift curve (ESC) positivity mapping with a value of $\alpha=10$ and without bias correction. FIG. 4D shows a reconstructed image using an ESC positivity mapping with a value of $\alpha=10$ and with bias correction. FIG. 4F shows a reconstructed image using an exponential shift curve (ESC) positivity mapping with a value of $\alpha=20$ and without bias correction. FIG. 4G shows a reconstructed image using an ESC positivity mapping with a value of $\alpha=20$ and with bias correction.

Each of FIGS. 4A, 4B, 4C, 4D, 4E, and 4F shows a circled region for which the mean attenuation and the standard deviation have been calculated. The reconstructed images are in Hounsfield units (HU) and the background of the phantom is water corresponding to an attenuation value of zero HU. The mean and standard deviation results for the circled regions in FIGS. 4A, 4B, 4C, 4D, 4E, and 4F are shown in Table 1. It can be observed that the methods with bias correction produce a mean attenuation much closer to the true value of 0 HU for the water phantom. Although the method with sinogram smoothing shown in FIG. 4B also improves the CT quantitative accuracy, it does so at the expense of decreasing the resolution of the reconstructed image.

TABLE 1

Mean and standard deviation results for the circled regions in FIGS. 4A, 4B, 4C, 4D, 4E, and 4F.

| FIG. | Method | Mean | STD |
|---|---|---|---|
| 4A | Log-tweak | −19.2 | 217.4 |
| 4B | Log-tweak + smoothing | −18.8 | 30.0 |
| 4C | a = 10 w/o BC | −43.6 | 192.9 |
| 4D | a = 10 w/BC | −0.2 | 195.7 |
| 4E | a = 20 w/o BC | −103.4 | 143.4 |
| 4F | a = 20 w/BC | 1.4 | 148.5 |

Figure 5A:
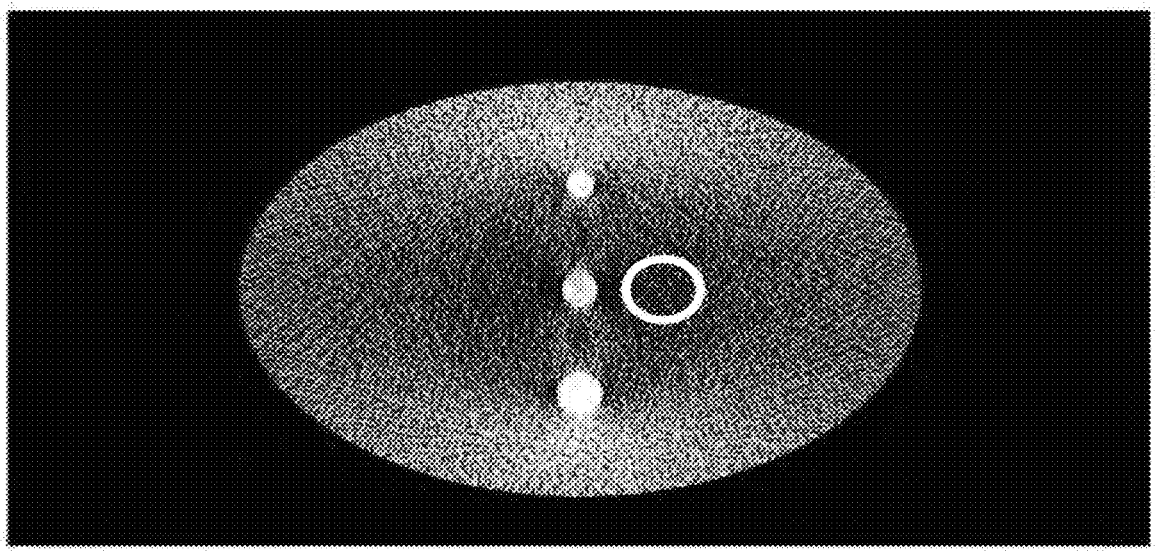
FIG. 5A shows a reconstructed image of a water phantom with bone inserts using a log-tweak positivity mapping, wherein the data is acquired using an X-ray tube current of 10 mAs.
Figure 5B:
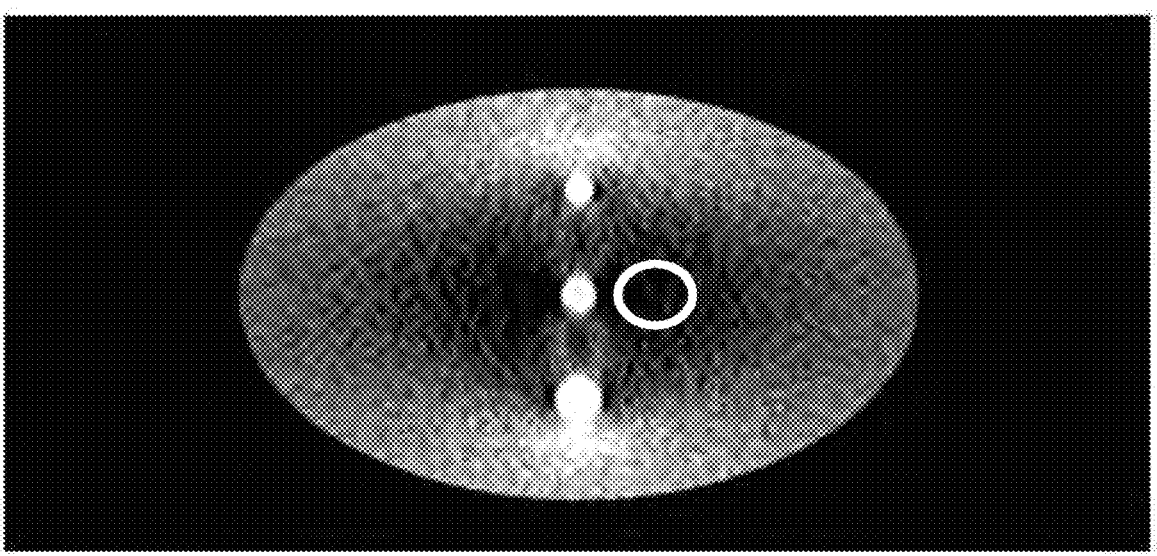
FIG. 5B shows a reconstructed image of a water phantom with bone inserts using sinogram smoothing and a log-tweak positivity mapping, wherein the data is acquired using an X-ray tube current of 10 mAs.
Figure 5C:
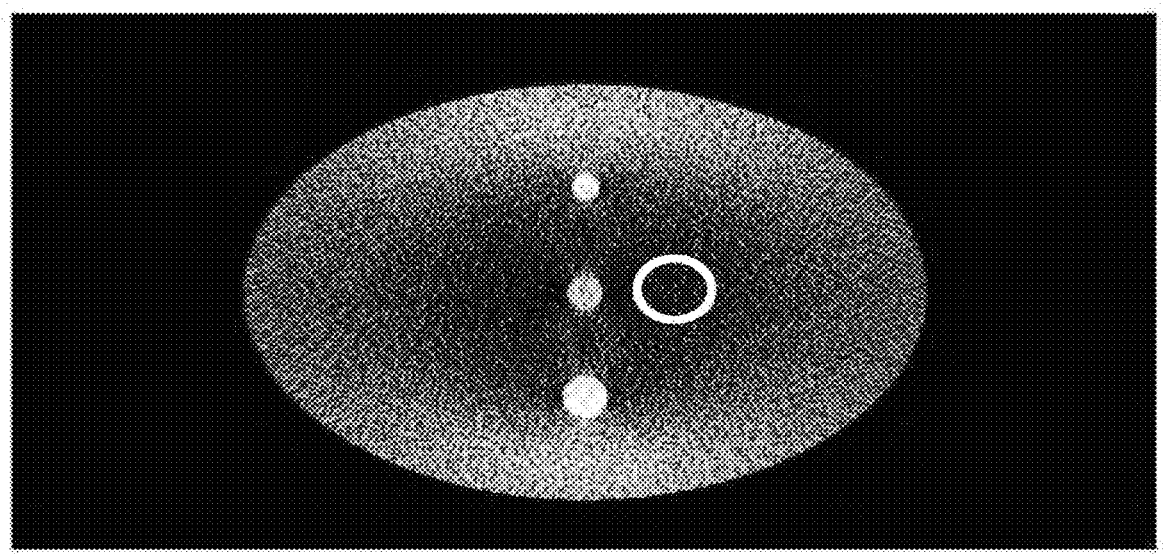
FIG. 5C shows a reconstructed image of a water phantom with bone inserts using an ESC positivity mapping with a value of $\alpha=10$ and without bias correction, wherein the data is acquired using an X-ray tube current of 10 mAs.
Figure 5D:
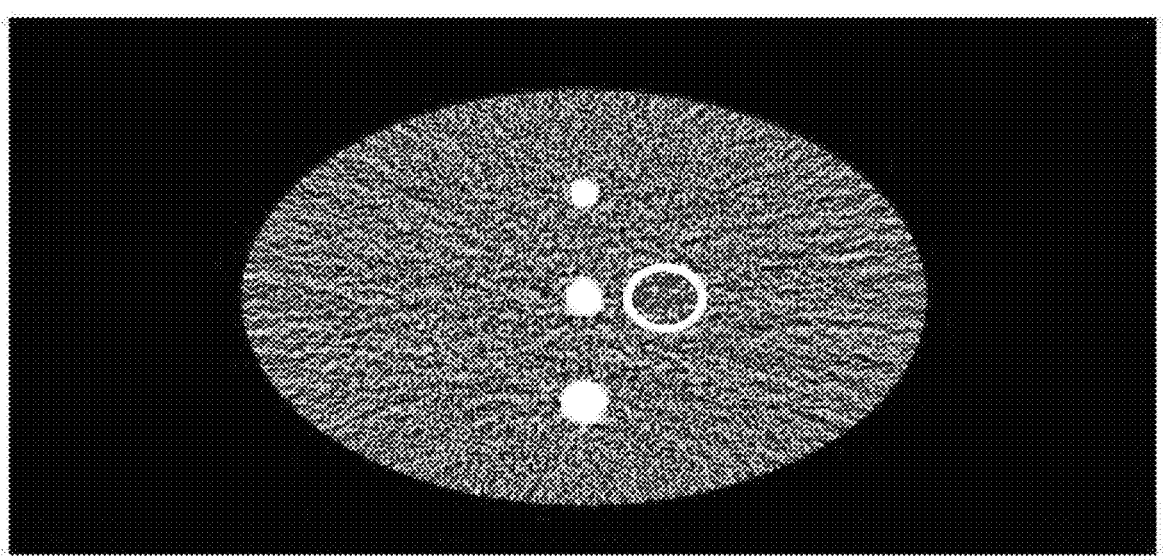
FIG. 5D shows a reconstructed image of a water phantom with bone inserts using an ESC positivity mapping with a value of $\alpha=10$ and with bias correction, wherein the data is acquired using an X-ray tube current of 10 mAs.
Figure 5E:
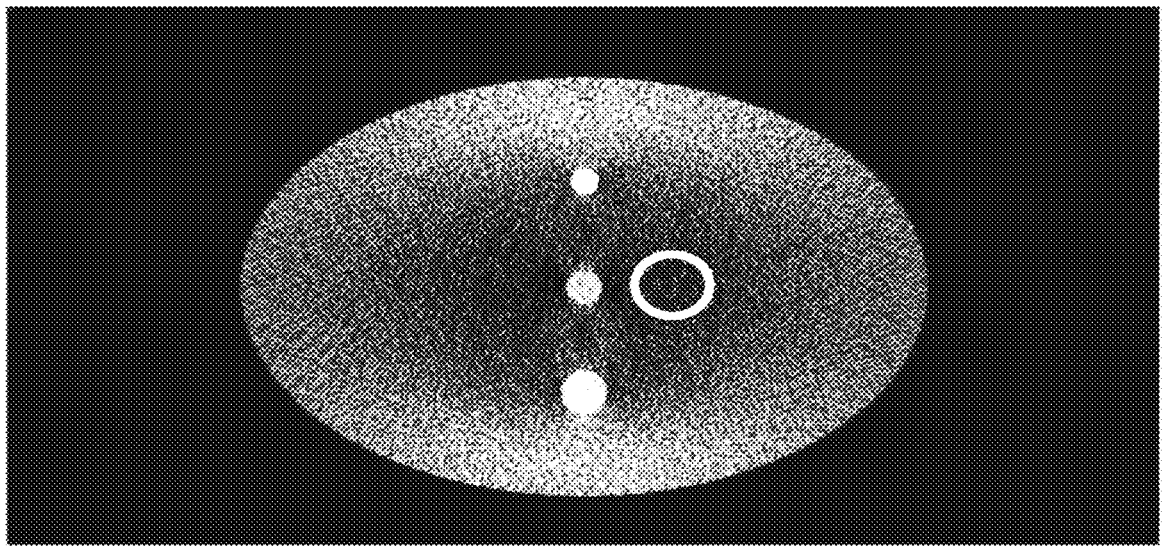
FIG. 5E shows a reconstructed image of a water phantom with bone inserts using an ESC positivity mapping with a value of $\alpha=20$ and without bias correction, wherein the data is acquired using an X-ray tube current of 10 mAs.
Figure 5F:
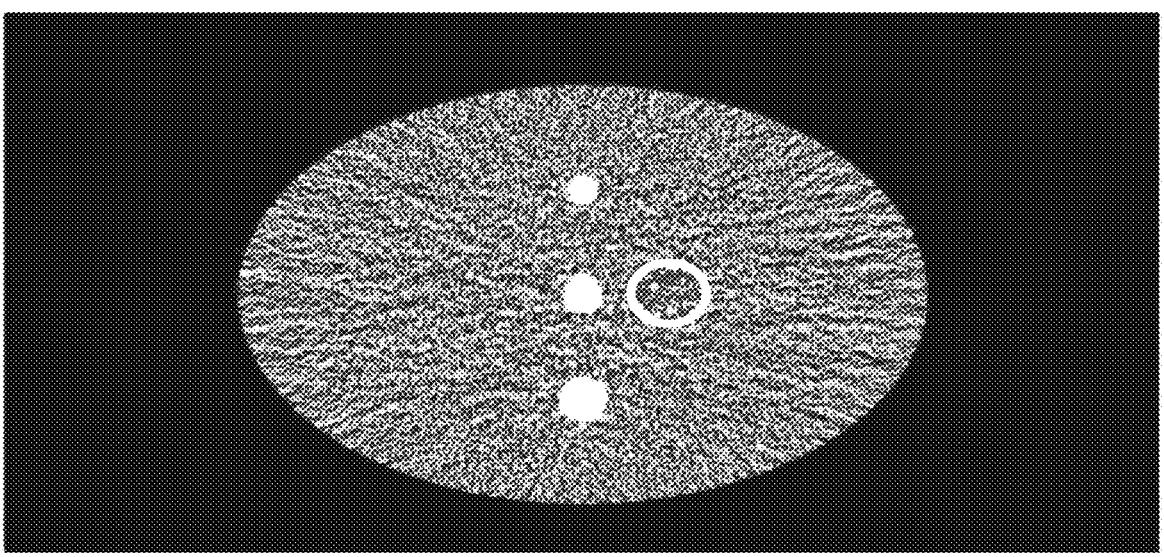
FIG. 5F shows a reconstructed image of a water phantom with bone inserts using an ESC positivity mapping with a value of $\alpha=20$ and with bias correction, wherein the data is acquired using an X-ray tube current of 10 mAs.

FIGS. 5A, 5B, 5C, 5D, 5E, and 5F show reconstructed images generated from projection data acquired also using the water phantom with bone inserts. The voltage across the X-ray tube is 80 kVp and the current was 10 mAs, which is significantly lower than the current used in FIGS. 4A through 4F resulting in a commensurate reduction in the count level. Accordingly, the effects of low-count level and the accompanying bias due to the positivity mapping are more pronounced. Figure 5A shows a reconstructed image using a log-tweak positivity mapping without bias correction. FIG. 5B shows a reconstructed image using sinogram denoising/smoothing together with a log-tweak positivity mapping without bias correction. FIG. 5C shows a reconstructed image using an exponential shift curve (ESC) positivity mapping with a value of $\alpha=10$ and without bias correction. FIG. 5D shows a reconstructed image using an ESC positivity mapping with a value of $\alpha=10$ and with bias correction. FIG. 5F shows a reconstructed image using an ESC positivity mapping with a value of $\alpha=20$ and without bias correction. FIG. 5G shows a reconstructed image using an ESC positivity mapping with a value of $\alpha=20$ and with bias correction.

Each of FIGS. 5A, 5B, 5C, 5D, 5E, and 5F shows a circled region for which the mean attenuation and the standard deviation have been calculated. The mean and standard deviation results for the circled regions in FIGS. 5A, 5B, 5C, 5D, 5E, and 5F are shown in Table 2. It can be observed that the methods with bias correction produce a mean attenuation much closer to the true value of 0 HU. Further, although the method with sinogram smoothing shown in FIG. 5B also improves the CT quantitative accuracy, it does so at the expense of decreasing the resolution of the reconstructed image. At the lower count level, the effects of the bias artifact are much more visible in FIGS. 5A, 5B, 5C, 5D, 5E, and 5F than in FIGS. 4A, 4B, 4C, 4D, 4E, and 4F.

TABLE 2

Mean and standard deviation results for the circled regions in FIGS. 5A, 5B, 5C, 5D, 5E, and 5F.

| FIG. | Method | Mean | STD |
|---|---|---|---|
| 5A | Log-tweak | −176.6 | 224.5 |
| 5B | Log-tweak + smoothing | −175.5 | 36.0 |
| 5C | a = 10 w/o BC | −220.2 | 196.8 |
| 5D | a = 10 w/BC | −5.9 | 223.1 |
| 5E | a = 20 w/o BC | −334.3 | 115.4 |
| 5F | a = 20 w/BC | −3.0 | 154.6 |

Figure 6A:
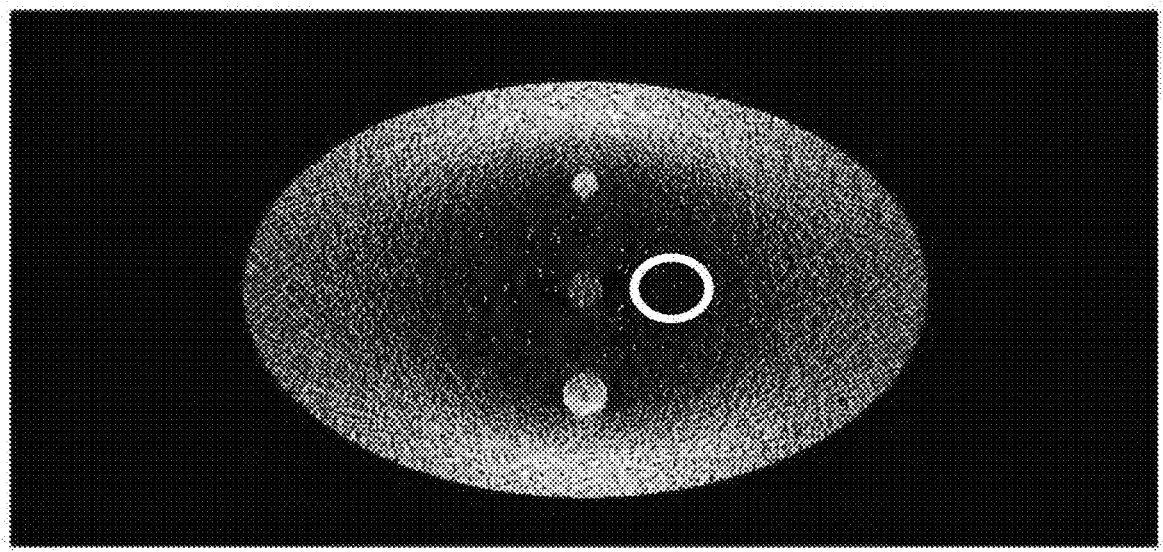
FIG. 6A shows a reconstructed image of a water phantom with bone inserts using a log-tweak positivity mapping, wherein the data is acquired using an X-ray tube current of 5 mAs.
Figure 6B:
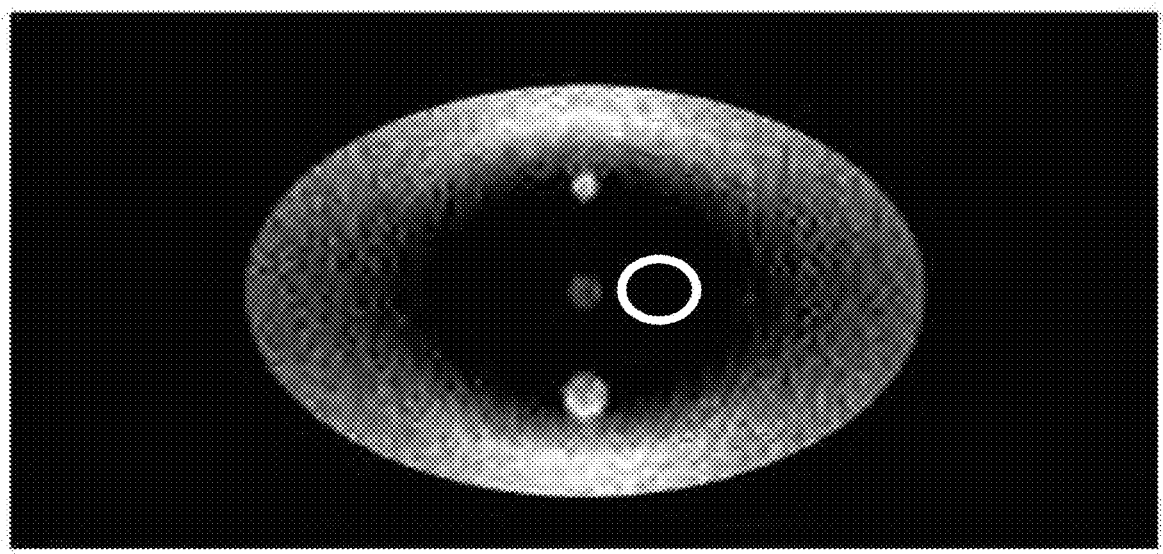
FIG. 6B shows a reconstructed image of a water phantom with bone inserts using sinogram smoothing and a log-tweak positivity mapping, wherein the data is acquired using an X-ray tube current of 5 mAs.
Figure 6C:
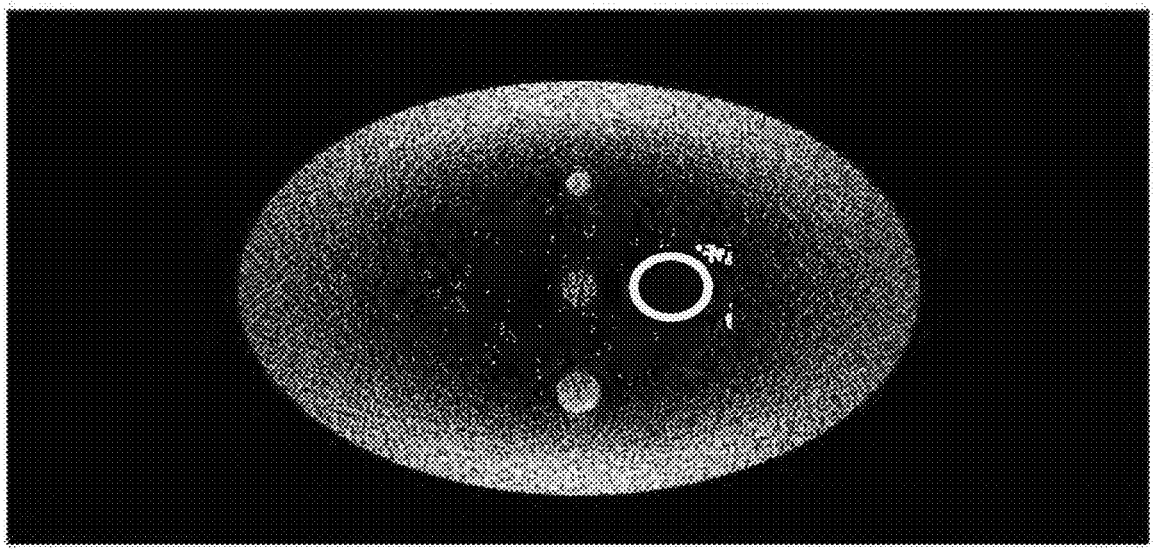
FIG. 6C shows a reconstructed image of a water phantom with bone inserts using an ESC positivity mapping with a value of α=10 and without bias correction, wherein the data is acquired using an X-ray tube current of 5 mAs.
Figure 6D:
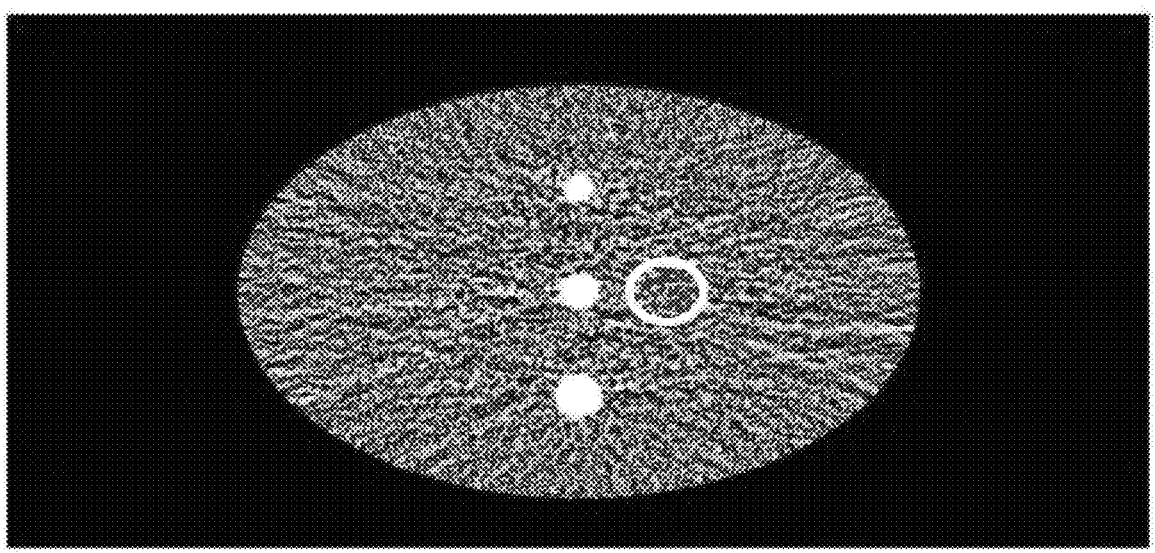
FIG. 6D shows a reconstructed image of a water phantom with bone inserts using an ESC positivity mapping with a value of α=10 and with bias correction, wherein the data is acquired using an X-ray tube current of 5 mAs.
Figure 6E:
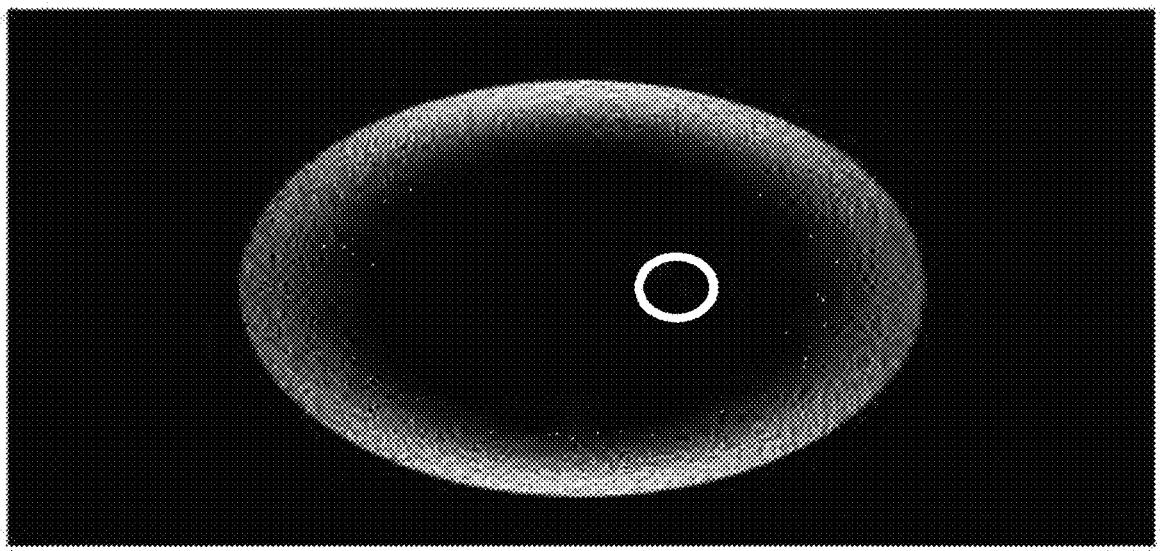
FIG. 6E shows a reconstructed image of a water phantom with bone inserts using an ESC positivity mapping with a value of α=20 and without bias correction, wherein the data is acquired using an X-ray tube current of 5 mAs.
Figure 6F:
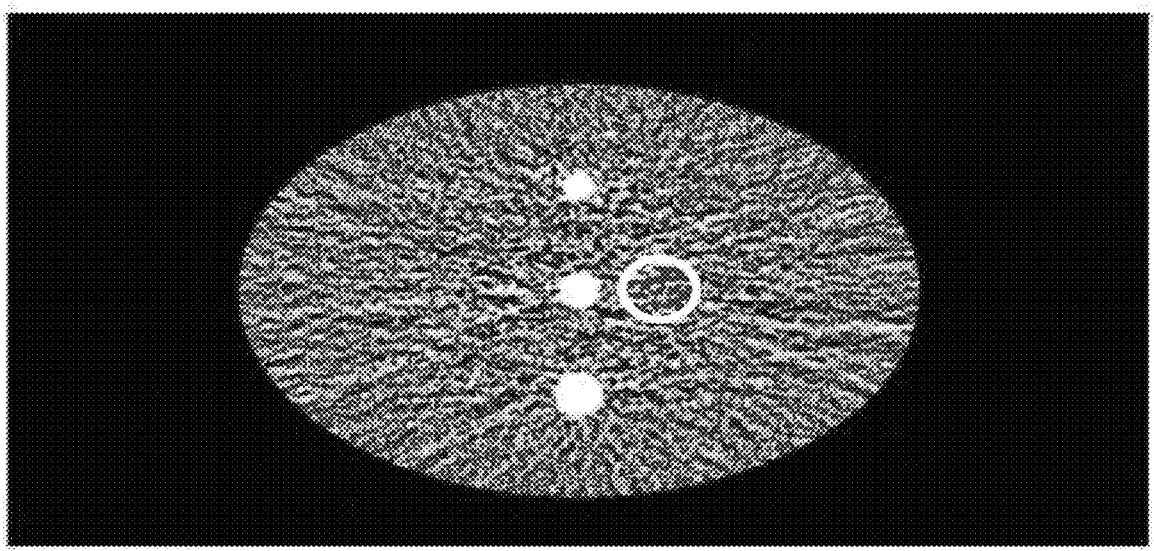
FIG. 6F shows a reconstructed image of a water phantom with bone inserts using an ESC positivity mapping with a value of α=20 and with bias correction, wherein the data is acquired using an X-ray tube current of 5 mAs.

FIGS. 6A, 6B, 6C, 6D, 6E, and 6F show reconstructed images generated from projection data acquired also using the water phantom with bone inserts. The voltage across the X-ray tube is 80 kVp and the current was 5 mAs, which is significantly lower than the current used in FIGS. 4A through 4F and FIGS. 5A through 5F. Accordingly, the effects of low-count level and the accompanying bias due to the positivity mapping are more pronounced. FIG. 6A shows a reconstructed image using a log-tweak positivity mapping without bias correction. FIG. 6B shows a reconstructed image using sinogram denoising/smoothing together with a log-tweak positivity mapping without bias correction. FIG. 6C shows a reconstructed image using an exponential shift curve (ESC) positivity mapping with a value of α=10 and without bias correction. FIG. 6D shows a reconstructed image using an ESC positivity mapping with a value of α=10 and with bias correction. FIG. 6F shows a reconstructed image using an ESC positivity mapping with a value of α=20 and without bias correction. FIG. 6G shows a reconstructed image using an ESC positivity mapping with a value of α=20 and with bias correction.

TABLE 3

Mean and standard deviation results for the circled regions in FIGS. 6A, 6B, 6C, 6D, 6E, and 6F.

| FIG. | Method | Mean | STD |
|---|---|---|---|
| 6A | Log-tweak | −304.0 | 164.3 |
| 6B | Log-tweak + smoothing | −300.7 | 27.5 |
| 6C | a = 10 w/o BC | −343.8 | 155.9 |
| 6D | a = 10 w/BC | −6.7 | 203.4 |
| 6E | a = 20 w/o BC | −460.8 | 84.3 |
| 6F | a = 20 w/BC | −4.2 | 151.0 |

Each of FIGS. 6A, 6B, 6C, 6D, 6E, and 6F shows a circled region for which the mean attenuation and the standard deviation have been calculated. The mean and standard deviation results for the circled regions in FIGS. 6A, 6B, 6C, 6D, 6E, and 6F are shown in Table 3. It can be observed that the methods with bias correction produce a mean attenuation value much closer to the true value of 0 HU. Further, although the method with sinogram smoothing shown in FIG. 5B also improves the CT quantitative accuracy, it does so at the expense of decreasing the resolution of the reconstructed image. At the lower count level, the effects of the bias artifact are much more visible in FIGS. 5A, 5B, 5C, 5D, 5E, and 5F than in FIGS. 4A, 4B, 4C, 4D, 4E, and 4F.

Figure 7:
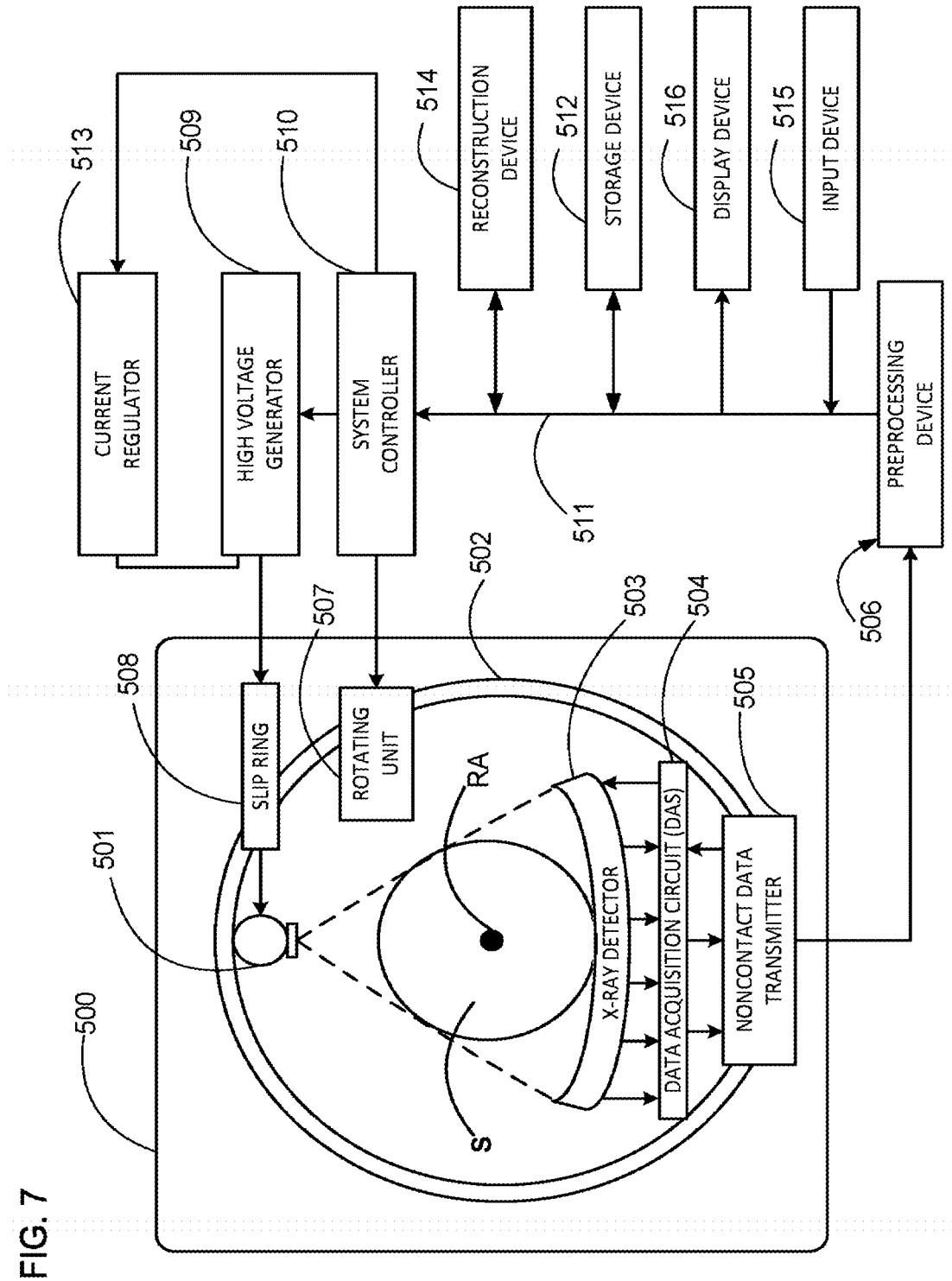
FIG. 7 shows a schematic of an implementation of a CT scanner, according to one implementation.

FIG. 7 illustrates an implementation of the radiography gantry included in a CT apparatus or scanner. As shown in FIG. 7, a radiography gantry 500 is illustrated from a side view and further includes an X-ray tube 501, an annular frame 502, and a multi-row or two-dimensional-array-type X-ray detector 503. The X-ray tube 501 and X-ray detector 503 are diametrically mounted across an object OBJ on the annular frame 502, which is rotatably supported around a rotation axis RA. A rotating unit 507 rotates the annular frame 502 at a high speed, such as 0.4 sec/rotation, while the object OBJ is being moved along the axis RA into or out of the illustrated page.

The first embodiment of an X-ray computed tomography (CT) apparatus according to the present inventions will be described below with reference to the views of the accompanying drawing. Note that X-ray CT apparatuses include various types of apparatuses, e.g., a rotate/rotate-type apparatus in which an X-ray tube and X-ray detector rotate together around an object to be examined, and a stationary/rotate-type apparatus in which many detection elements are arrayed in the form of a ring or plane, and only an X-ray tube rotates around an object to be examined. The present inventions can be applied to either type. In this case, the rotate/rotate type, which is currently the mainstream, will be exemplified.

The multi-slice X-ray CT apparatus further includes a high voltage generator 509 that generates a tube voltage applied to the X-ray tube 501 through a slip ring 508 so that the X-ray tube 501 generates X-rays. The X-rays are emitted towards the object OBJ, whose cross sectional area is represented by a circle. For example, the X-ray tube 501 having an average X-ray energy during a first scan that is less than an average X-ray energy during a second scan. Thus, two or more scans can be obtained corresponding to different X-ray energies. The X-ray detector 503 is located at an opposite side from the X-ray tube 501 across the object OBJ for detecting the emitted X-rays that have transmitted through the object OBJ. The X-ray detector 503 further includes individual detector elements or units.

The CT apparatus further includes other devices for processing the detected signals from X-ray detector 503. A data acquisition circuit or a Data Acquisition System (DAS) 504 converts a signal output from the X-ray detector 503 for each channel into a voltage signal, amplifies the signal, and further converts the signal into a digital signal. The X-ray detector 503 and the DAS 504 are configured to handle a predetermined total number of projections per rotation (TPPR).

The above-described data is sent to a preprocessing device 506, which is housed in a console outside the radiography gantry 500 through a non-contact data transmitter 505. The preprocessing device 506 performs certain corrections, such as sensitivity correction on the raw data. A memory 512 stores the resultant data, which is also called projection data at a stage immediately before reconstruction processing. The memory 512 is connected to a system controller 510 through a data/control bus 511, together with a reconstruction device 514, input device 515, and display 516. The system controller 510 controls a current regulator 513 that limits the current to a level sufficient for driving the CT system.

The detectors are rotated and/or fixed with respect to the patient among various generations of the CT scanner systems. In one implementation, the above-described CT system can be an example of a combined third-generation geometry and fourth-generation geometry system. In the third-generation system, the X-ray tube 501 and the X-ray detector 503 are diametrically mounted on the annular frame 502 and are rotated around the object OBJ as the annular frame 502 is rotated about the rotation axis RA. In the fourth-generation geometry system, the detectors are fixedly placed around the patient and an X-ray tube rotates around the patient. In an alternative embodiment, the radiography gantry 500 has multiple detectors arranged on the annular frame 502, which is supported by a C-arm and a stand.

The memory 512 can store the measurement value representative of the irradiance of the X-rays at the X-ray detector unit 503. Further, the memory 512 can store a dedicated program for executing method 100 and method 200 for correcting low-count data and CT image reconstruction.

The reconstruction device 514 can execute method 100 and method 200. Further, reconstruction device 514 can execute pre-reconstruction processing image processing such as volume rendering processing and image difference processing as needed.

The pre-reconstruction processing of the projection data performed by the preprocessing device 506 can include correcting for detector calibrations, detector nonlinearities, and polar effects, for example. Further, the pre-reconstruction processing can include various steps of method 100 and method 200.

Post-reconstruction processing performed by the reconstruction device 514 can include filtering and smoothing the image, volume rendering processing, and image difference processing as needed. The image reconstruction process can implement various of the steps of method 100 and method 200 in addition to various CT image reconstruction methods. The reconstruction device 514 can use the memory to store, e.g., projection data, reconstructed images, calibration data and parameters, and computer programs.

The reconstruction device 514 can include a CPU (processing circuitry) that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory 512 can be non-volatile, such as ROM, EPROM, EEPROM or FLASH memory. The memory 512 can also be volatile, such as static or dynamic RAM, and a processor, such as a microcontroller or microprocessor, can be provided to manage the electronic memory as well as the interaction between the FPGA or CPLD and the memory.

Alternatively, the CPU in the reconstruction device 514 can execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed images can be displayed on a display 516. The display 516 can be an LCD display, CRT display, plasma display, OLED, LED or any other display known in the art.

The memory 512 can be a hard disk drive, CD-ROM drive, DVD drive, FLASH drive, RAM, ROM or any other electronic storage known in the art.

While certain implementations have been described, these implementations have been presented by way of example only, and are not intended to limit the teachings of this disclosure. Indeed, the novel methods, apparatuses and systems described herein may be embodied in a variety of other forms; furthermore, various omissions, substitutions and changes in the form of the methods, apparatuses and systems described herein may be made without departing from the spirit of this disclosure.

The invention claimed is:

1. An apparatus, comprising:
    processing circuitry configured to
        obtain projection data representing an intensity of X-ray radiation detected at a plurality of detector elements after traversing an object, the projection data being corrected for a baseline offset,
        correct the projection data by performing a positivity mapping to generate corrected projection data,
        perform a logarithm operation on the corrected projection data to generate post-log projection data,
        correct the post-log projection data for a bias of the post-log projection data, using the projection data, to generate bias-corrected projection data, and
        reconstruct an image of the object using the bias-corrected projection data, wherein
    the projection data is linearly related to an exponential of an attenuation coefficient of the X-ray radiation and the post-log projection data is linearly related to the attenuation coefficient of the X-ray radiation.

2. The apparatus according to claim 1, wherein the processing circuitry is further configured to
    estimate the bias of the post-log projection data using a probability density function of noise associated with the intensity of X-ray radiation detected at one or more of the plurality of detector elements, and
    generate a look-up table relating a mean value of the projection data to a bias-correction value for the logarithm operation and the positivity mapping, the bias-correction value corresponding to the estimated bias of the post-log projection data.

3. The apparatus according to claim 2, wherein the processing circuitry is further configured to generate the look-up table by
    obtaining calibration data representing an intensity of the X-ray radiation detected at the plurality of detector elements during a calibration scan, the calibration data being corrected for the baseline offset and representing the X-ray radiation generated with a plurality of settings of an X-ray source generating the X-ray radiation,
    determining respective mean count values of the calibration data, for each detector element of the plurality of detector elements and for each setting of the plurality of settings of the X-ray source, and generate post-log mean count values by performing the logarithm operation on the respective mean count values,
    determining post-log calibration data by performing the positivity mapping and the logarithm operation on the calibration data,
    determining bias-correction values representing respective differences between respective expectation values of the post-log calibration data and the corresponding post-log mean count values, the bias-correction values corresponding to the estimated bias of the post-log projection that is estimated using the probability density function derived from the calibration data, and associating the respective bias-correction values with the corresponding mean count values to generate the look-up table.

4. The apparatus according to claim 2, wherein the processing circuitry is further configured to generate the look-up table by obtaining the probability density function of noise using a statistical model of the X-ray radiation detected at the plurality of detector elements, determining bias-correction values corresponding to the estimated bias of the post-log projection data and representing respective differences between expectation values of post-log data and logarithms of true values, wherein each of the expectation values of post-log data include an expectation value integral over the probability density function with an integrand that includes the logarithm operation of the positivity mapping of a value representing the detected X-ray radiation, and associating the respective bias-correction values with the corresponding true values to generate the look-up table.

5. The apparatus according to claim 4, wherein the processing circuitry is further configured to generate the look-up table by obtaining the probability density function representing the statistical model that is one of a linear combination of a compound Poison model and Gaussian model, a shifted Poisson model, a linear combination of a Poisson model and Gaussian model, a mixture model, a Poisson model, and a Gaussian model.

6. The apparatus according to claim 1, wherein the processing circuitry is further configured to perform the positivity mapping, which is one of a threshold method, an absolute-value method, an exponential shift curve method, a log-tweak method, and a Maximum-likelihood based method.

7. The apparatus according to claim 1, wherein the processing is further configured to correct the post-log projection data for the bias of the post-log projection data by estimating the bias of the post-log projection data using a probability density function of noise associated with the intensity of X-ray radiation detected at one or more of the plurality of detector elements, using a look-up table to look up respective bias values associated with corresponding values of the projection data, wherein, when the look-up table receives an input of a value of the pre-log projection data, the look-up table outputs an associated bias value, and subtract the respective bias values from the corresponding post-log projection data to generate the bias-corrected projection data.

8. The apparatus according to claim 7, wherein the processing circuitry is further configured to denoise the projection data to generate denoised projection data, estimate a mean value for each of the plurality of detector elements using the denoised projection data, and input the mean value into the look-up table to generate outputs of the corresponding bias values.

9. The apparatus according to claim 8, wherein the processing circuitry is further configured to denoise the projection data by performing one of a low-pass filtering method, a linear-smoothing filtering method, an anisotropic diffusion method, a non-local means method, a sinogram restoration method, a local linear minimum mean-squared-error filtering method, a Gaussian estimator method, a count adaptive mean estimator, and a nonlinear filtering method.

10. The apparatus according to claim 1, wherein the processing circuitry is further configured to bypass the correcting of the projection data by performing a positivity mapping and the correcting for the bias of the post-log projection data, for values of the projection data that exceed a predefined threshold.

11. The apparatus according to claim 1, wherein the processing circuitry is further configured to correct the projection data by performing a scatter correction on the projection data to separate the projection data into primary data and scattered data, and performing a positivity mapping on the primary data to generate the corrected projection data.

12. The apparatus according to claim 1, wherein the processing circuitry is further configured to perform a beam-hardening correction on the bias-corrected projection data to generate beam-hardening corrected data, and reconstruct the image using the beam-hardening corrected data and using one of an iterated reconstruction method, an iterated reconstruction method using a regularization term, and a filtered back-projection method.

13. The apparatus according to claim 1, wherein the processing circuitry is further configured to refine the bias-corrected projection data by performing an exponential operation on the bias-corrected projection data to generate another projection data, correcting the another projection data by performing the positivity mapping to generate another corrected projection data, performing the logarithm operation on the another corrected projection data to generate another post-log projection data, and correcting for a bias of the another post-log projection data, using the projection data, to generate another bias-corrected projection data, wherein the image of the object is reconstructed using the another bias-corrected projection data.

14. An apparatus, comprising:

an X-ray source to radiate X-rays;

a plurality of detector elements, each configured to
detect the X-ray radiation emanating from the X-ray source, after the X-ray radiation traverses an object, and generate projection data representing an intensity of the X-rays detected at the plurality of detector elements, wherein the projection data is corrected for a baseline offset; and processing circuitry configured to
correct the projection data by performing a positivity mapping to generate corrected projection data, perform a logarithm operation on the corrected projection data to generate post-log projection data, correct the post-log projection data for a bias of the post-log projection data, using the projection data, to generate bias-corrected projection data, and reconstruct an image of the object from the bias-corrected projection data, wherein the projection data is linearly related to an exponential of an attenuation coefficient of the X-ray radiation and the post-log projection data is linearly related to the attenuation coefficient of the X-ray radiation.

15. The apparatus according to claim 14, wherein the bias of the post-log projection data is estimated using a probability density function for noise associated with the intensity of X-ray radiation detected at one or more of the plurality of detector elements.

16. A method, comprising:
obtaining projection data representing an intensity of X-ray radiation detected at a plurality of detector elements after traversing an object, the projection data being corrected for a baseline offset,
correcting the projection data by performing a positivity mapping to generate corrected projection data,
performing a logarithm operation on the corrected projection data to generate post-log projection data,
correcting the post-log projection data for a bias of the post-log projection data, using the projection data, to generate bias-corrected projection data, and
reconstructing an image of the object from the bias-corrected projection data, wherein
the projection data is linearly related to an exponential of an attenuation coefficient of the X-ray radiation and the post-log projection data is linearly related to the attenuation coefficient of the X-ray radiation.

17. The method according to claim 16, further comprising:
estimating the bias of the post-log projection data using a probability density function of noise associated with the intensity of X-ray radiation detected at one or more of the plurality of detector elements, and
generating a look-up table relating respective values of the projection data to bias-correction values, the bias-correction values corresponding to the estimated bias of the post-log projection data.

18. The method according to claim 17, wherein the generating of the look-up table further includes
obtaining calibration data representing an intensity of the X-ray radiation detected at the plurality of detector elements during a calibration scan, the calibration data being corrected for the baseline offset and representing the X-ray radiation generated with a plurality of settings of an X-ray source generating the X-ray radiation,
determining respective mean count values of the calibration data, for each detector element of the plurality of detector elements and for each setting of the plurality of settings of the X-ray source, and generate post-log mean count values by performing the logarithm operation on the respective mean count values,
determining post-log calibration data by performing the positivity mapping and the logarithm operation on the calibration data,
determining bias-correction values representing respective differences between respective expectation values of the post-log calibration data and the corresponding post-log mean count values, the bias-correction values corresponding to the bias of the post-log projection estimated using the probability density function derived from the calibration data, and
associating the respective bias-correction values with the corresponding mean count values to generate the look-up table.

19. The method according to claim 17, wherein the generating of the look-up table further includes
obtaining the probability density function for noise using a statistical model of the X-ray radiation detected at the plurality of detector elements,
determining bias-correction values corresponding to the estimated bias of the post-log projection data and representing respective differences between expectation values of post-log data and logarithms of true values, wherein each of the expectation values of post-log data include an expectation value integral over the probability density function with an integrand that includes the logarithm operation of the positivity mapping of a value representing the detected X-ray radiation, and
associating the respective bias-correction values with the corresponding true values to generate the look-up table.

20. The method according to claim 16, wherein the correcting the post-log projection data includes
estimating the bias of the post-log projection data using a probability density function of noise associated with the intensity of X-ray radiation detected at one or more of the plurality of detector elements,
correcting for the bias of the post-log projection data using a look-up table to look up respective bias values associated with corresponding values of the projection data, the bias values corresponding to the estimated bias of the post-log projection data, wherein, when the look-up table receives an input of a pre-log projection data value, the look-up table outputs an associated bias value, and
subtracting the respective bias values from the corresponding post-log projection data to generate the bias-corrected projection data.

21. A non-transitory computer readable storage medium including executable instruction, wherein the instructions, when executed by circuitry, cause the circuitry to perform the method according to claim 16.

* * * * *